United States Patent
Lesh

(10) Patent No.: US 7,044,135 B2
(45) Date of Patent: *May 16, 2006

(54) DEVICE AND METHOD FOR FORMING A CIRCUMFERENTIAL CONDUCTION BLOCK IN A PULMONARY VEIN

(75) Inventor: Michael D. Lesh, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 209 days.

This patent is subject to a terminal disclaimer.

(21) Appl. No.: 10/233,157

(22) Filed: Aug. 30, 2002

(65) Prior Publication Data

US 2003/0065307 A1    Apr. 3, 2003

Related U.S. Application Data

(63) Continuation of application No. 09/642,251, filed on Aug. 17, 2000, now Pat. No. 6,502,576, which is a continuation of application No. 09/384,727, filed on Aug. 27, 1999, now Pat. No. 6,305,378, which is a continuation of application No. 08/889,835, filed on Jul. 8, 1997, now Pat. No. 6,012,457, and a continuation-in-part of application No. 09/357,184, filed on Jul. 19, 1999, now Pat. No. 6,471,697, which is a continuation of application No. 08/853,861, filed on May 9, 1997, now Pat. No. 5,971,983.

(51) Int. Cl.
*A61B 19/00* (2006.01)

(52) U.S. Cl. ..................................... 128/898
(58) Field of Classification Search .............. 128/898; 604/96.01, 113, 114, 97.01; 606/41, 45, 606/47; 607/62, 122, 125, 126, 130
See application file for complete search history.

(56) References Cited

U.S. PATENT DOCUMENTS 3,565,062 A    2/1971 Kurls (Continued)

FOREIGN PATENT DOCUMENTS

DE    296 09 350 U1    8/1996

(Continued)

OTHER PUBLICATIONS

Avitall, Boaz et al.; "Physics and Engineering of Transcatheter Ardiac Tissue Ablation," JACC, vol. 22, No. 3, pp. 921-932, Sep., 1993.

(Continued)

*Primary Examiner*—Corrine McDermott
*Assistant Examiner*—William H Matthews
(74) *Attorney, Agent, or Firm*—John P. O'Banion

(57) ABSTRACT

This invention is a method for treating a patient diagnosed with atrial arrhythmia by forming a circumferential conduction block along a circumferential path of tissue in a pulmonary vein wall that circumscribes the pulmonary vein lumen and transects the electrical conductivity of the pulmonary vein such that conduction is blocked along the longitudinal axis of the vein wall and into the left atrial wall. The method is performed to treat a patient with a focal arrythmogenic origin along the pulmonary vein wall by either ablating the focal origin or by isolating the focal origin from the atrial wall with the circumferential conduction block. The circumferential conduction block is also formed in a pulmonary vein in order to bridge the adjacent ends of two linear lesions, wherein each linear lesion is formed to extend between the pulmonary vein and another adjacent pulmonary vein in a less-invasive "maze"-type procedure. A circumferential ablation element in a circumferential ablation device assembly is used in a percutaneous translumenal catheter technique in order to form the circumferential conduction block in the pulmonary vein wall.

32 Claims, 19 Drawing Sheets

U.S. PATENT DOCUMENTS

| | | |
|---|---|---|
| 3,938,502 A | 2/1976 | Bom |
| 4,316,472 A | 2/1982 | Mirowski et al. |
| 4,354,497 A | 10/1982 | Kahn |
| 4,411,266 A | 10/1983 | Cosman |
| 4,449,528 A | 5/1984 | Auth et al. |
| 4,522,205 A | 6/1985 | Taylor et al. |
| 4,565,200 A | 1/1986 | Cosman |
| 4,569,801 A | 2/1986 | Molloy et al. |
| 4,616,333 A | 10/1986 | Shimoni |
| 4,637,392 A | 1/1987 | Sorochenko |
| 4,641,649 A | 2/1987 | Walinsky et al. |
| 4,660,571 A | 4/1987 | Hess et al. |
| 4,662,368 A | 5/1987 | Hussein et al. |
| 4,669,469 A | 6/1987 | Gifford, III et al. |
| 4,672,962 A | 6/1987 | Hershenson |
| 4,673,563 A | 6/1987 | Berne et al. |
| 4,676,258 A | 6/1987 | Inokuchi et al. |
| 4,699,147 A | 10/1987 | Chilson et al. |
| 4,757,820 A | 7/1988 | Itoh |
| 4,762,129 A | 8/1988 | Bonzel |
| 4,790,311 A | 12/1988 | Ruiz |
| 4,790,317 A | 12/1988 | Davies |
| 4,799,493 A | 1/1989 | DuFault |
| 4,807,620 A | 2/1989 | Strul et al. |
| 4,841,977 A | 6/1989 | Griffith et al. |
| 4,882,777 A | 11/1989 | Narula |
| 4,898,591 A | 2/1990 | Jang et al. |
| 4,920,980 A | 5/1990 | Jackowski |
| 4,924,863 A | 5/1990 | Sterzer |
| 4,932,413 A | 6/1990 | Shockey et al. |
| 4,936,281 A | 6/1990 | Stasz |
| 4,940,064 A | 7/1990 | Desai |
| 4,945,912 A | 8/1990 | Langberg |
| 4,951,677 A | 8/1990 | Crowley et al. |
| 4,974,598 A | 12/1990 | John |
| 4,976,711 A | 12/1990 | Parins et al. |
| 4,998,933 A | 3/1991 | Eggers et al. |
| 5,000,185 A | 3/1991 | Yock |
| 5,002,059 A | 3/1991 | Crowley et al. |
| 5,007,908 A | 4/1991 | Rydell |
| 5,035,694 A | 7/1991 | Kasprzyk et al. |
| 5,058,599 A | 10/1991 | Andersen |
| 5,074,313 A | 12/1991 | Dahl et al. |
| 5,078,717 A | 1/1992 | Parihs et al. |
| 5,090,958 A | 2/1992 | Sahota |
| 5,103,821 A | 4/1992 | King |
| 5,104,393 A | 4/1992 | Isner et al. |
| 5,107,850 A | 4/1992 | Olive |
| 5,131,397 A | 7/1992 | Crowley |
| 5,147,355 A | 9/1992 | Friedman et al. |
| 5,156,157 A | 10/1992 | Valenta, Jr. et al. |
| 5,158,079 A | 10/1992 | Adams et al. |
| 5,178,618 A | 1/1993 | Kandarpa |
| 5,178,620 A | 1/1993 | Eggers et al. |
| 5,186,177 A | 2/1993 | O'Donnell et al. |
| 5,190,540 A | 3/1993 | Lee |
| 5,195,990 A | 3/1993 | Weldor |
| 5,209,229 A | 5/1993 | Gilli |
| 5,222,501 A | 6/1993 | Ideker et al. |
| 5,226,430 A | 7/1993 | Spears et al. |
| 5,228,442 A | 7/1993 | Imran |
| 5,231,994 A | 8/1993 | Harmjanz |
| 5,231,995 A | 8/1993 | Desai |
| 5,255,679 A | 10/1993 | Imran |
| 5,259,395 A | 11/1993 | Li |
| 5,263,493 A | 11/1993 | Avitall |
| 5,275,162 A | 1/1994 | Edwards et al. |
| 5,281,215 A | 1/1994 | Milder |
| 5,292,321 A | 3/1994 | Lee |
| 5,293,868 A | 3/1994 | Nardella |
| 5,293,869 A | 3/1994 | Edwards et al. |
| 5,295,484 A | 3/1994 | Marcus et al. |
| 5,300,085 A | 4/1994 | Yock |
| 5,311,873 A | 5/1994 | Savard et al. |
| 5,313,943 A | 5/1994 | Houser et al. |
| 5,314,460 A | 5/1994 | Borghi |
| 5,314,461 A | 5/1994 | Borghi |
| 5,324,255 A | 6/1994 | Passafaro et al. |
| 5,324,284 A | 6/1994 | Imran |
| 5,325,860 A | 7/1994 | Seward et al. |
| 5,331,966 A | 7/1994 | Bennett et al. |
| 5,336,222 A | 8/1994 | Durgin, Jr. et al. |
| 5,336,251 A | 8/1994 | Borghi |
| 5,342,292 A | 8/1994 | Nita et al. |
| 5,342,357 A | 8/1994 | Nardella |
| 5,344,435 A | 9/1994 | Turner et al. |
| 5,345,936 A | 9/1994 | Pomeranz et al. |
| 5,345,940 A | 9/1994 | Seward et al. |
| 5,348,554 A | 9/1994 | Imran et al. |
| 5,366,486 A | 11/1994 | Zipes et al. |
| 5,366,487 A | 11/1994 | Adams et al. |
| 5,366,490 A | 11/1994 | Edwards et al. |
| 5,368,035 A | 11/1994 | Hammet et al. |
| 5,368,557 A | 11/1994 | Nita et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Crowley et al. |
| 5,374,285 A | 12/1994 | Vaiani et al. |
| 5,383,876 A | 1/1995 | Nardella |
| 5,385,148 A | 1/1995 | Lesh et al. |
| 5,385,544 A | 1/1995 | Edwards et al. |
| 5,391,197 A | 2/1995 | Burdette et al. |
| 5,391,199 A | 2/1995 | Ben-Haim |
| 5,400,796 A | 3/1995 | Wecke |
| 5,403,311 A | 4/1995 | Abele et al. |
| 5,405,376 A | 4/1995 | Mulier et al. |
| 5,409,000 A | 4/1995 | Imran |
| 5,409,453 A | 4/1995 | Lundquist et al. |
| 5,411,524 A | 5/1995 | Rahul |
| 5,421,338 A | 6/1995 | Crowley et al. |
| 5,421,819 A | 6/1995 | Edwards et al. |
| 5,423,808 A | 6/1995 | Edwards et al. |
| 5,423,811 A | 6/1995 | Imran et al. |
| 5,427,119 A | 6/1995 | Swartz et al. |
| 5,431,649 A | 7/1995 | Mulier et al. |
| 5,433,198 A | 7/1995 | Desai |
| 5,433,708 A | 7/1995 | Nichols et al. |
| 5,435,805 A | 7/1995 | Edwards et al. |
| 5,437,664 A | 8/1995 | Cohen et al. |
| 5,439,483 A | 8/1995 | Duong-Van |
| 5,443,456 A | 8/1995 | Alliger et al. |
| 5,443,489 A | 8/1995 | Ben-Haim |
| 5,447,509 A | 9/1995 | Mills et al. |
| 5,449,380 A | 9/1995 | Chin |
| 5,450,846 A | 9/1995 | Goldreyer |
| 5,454,373 A | 10/1995 | Koger et al. |
| 5,456,682 A | 10/1995 | Edwards et al. |
| 5,464,431 A | 11/1995 | Adams et al. |
| 5,470,308 A | 11/1995 | Edwards et al. |
| 5,474,530 A | 12/1995 | Passafaro et al. |
| 5,476,503 A | 12/1995 | Yang |
| 5,482,037 A | 1/1996 | Borghi |
| 5,484,400 A | 1/1996 | Edwards et al. |
| 5,485,849 A | 1/1996 | Panescu et al. |
| 5,487,385 A | 1/1996 | Avitall |
| 5,496,312 A | 3/1996 | Klicek |
| 5,496,346 A | 3/1996 | Horzewski et al. |
| 5,496,360 A | 3/1996 | Hoffmann et al. |
| 5,497,774 A | 3/1996 | Swartz et al. |
| 5,498,238 A | 3/1996 | Shapland et al. |
| 5,500,012 A | 3/1996 | Brucker et al. |
| 5,501,227 A | 3/1996 | Yock |
| 5,505,702 A | 4/1996 | Arney |

| | | |
|---|---|---|
| 5,505,730 A | 4/1996 | Edwards |
| 5,507,802 A | 4/1996 | Imran |
| 5,509,900 A | 4/1996 | Kirkman |
| 5,522,873 A | 6/1996 | Jackman et al. |
| 5,540,679 A | 7/1996 | Fram et al. |
| 5,545,161 A | 8/1996 | Imran |
| 5,545,193 A | 8/1996 | Fleischman et al. |
| 5,549,603 A | 8/1996 | Feiring |
| 5,549,641 A | 8/1996 | Ayers et al. |
| 5,549,661 A | 8/1996 | Kordis et al. |
| 5,558,672 A | 9/1996 | Edwards et al. |
| 5,562,720 A | 10/1996 | Stern et al. |
| 5,564,440 A | 10/1996 | Swartz et al. |
| 5,571,088 A | 11/1996 | Lennox et al. |
| 5,571,159 A | 11/1996 | Alt |
| 5,575,766 A | 11/1996 | Swartz et al. |
| 5,575,772 A | 11/1996 | Lennox |
| 5,575,788 A | 11/1996 | Baker et al. |
| 5,575,810 A | 11/1996 | Swanson et al. |
| 5,582,609 A | 12/1996 | Swanson et al. |
| 5,588,432 A | 12/1996 | Crowley |
| 5,605,159 A | 2/1997 | Smith et al. |
| 5,606,974 A | 3/1997 | Castellano et al. |
| 5,607,422 A | 3/1997 | Smeets et al. |
| 5,607,462 A | 3/1997 | Imran |
| 5,609,151 A | 3/1997 | Mulier et al. |
| 5,617,854 A | 4/1997 | Munsif |
| 5,620,479 A | 4/1997 | Diederich |
| 5,630,837 A | 5/1997 | Crowley |
| 5,642,736 A | 7/1997 | Avitall |
| 5,645,082 A | 7/1997 | Sung et al. |
| 5,658,278 A | 8/1997 | Imran et al. |
| 5,661,133 A | 8/1997 | Leiden et al. |
| 5,673,695 A | 10/1997 | McGee et al. |
| 5,674,274 A | 10/1997 | Morgan et al. |
| 5,676,153 A | 10/1997 | Smith et al. |
| 5,676,662 A | 10/1997 | Fleischhacker et al. |
| 5,680,860 A | 10/1997 | Imran |
| 5,681,308 A | 10/1997 | Edwards et al. |
| 5,682,885 A | 11/1997 | Littmann et al. |
| 5,683,445 A | 11/1997 | Swoyer |
| 5,685,322 A | 11/1997 | Sung et al. |
| 5,685,839 A | 11/1997 | Edwards et al. |
| 5,687,723 A | 11/1997 | Avitall |
| 5,687,729 A | 11/1997 | Schaetzle |
| 5,688,267 A | 11/1997 | Panescu et al. |
| 5,690,611 A | 11/1997 | Swartz et al. |
| 5,693,078 A | 12/1997 | Desai et al. |
| 5,693,622 A | 12/1997 | Wolff et al. |
| 5,697,925 A | 12/1997 | Taylor |
| 5,697,927 A | 12/1997 | Imran et al. |
| 5,702,438 A | 12/1997 | Avitall |
| 5,715,818 A | 2/1998 | Swartz et al. |
| 5,716,389 A | 2/1998 | Walinsky et al. |
| 5,718,231 A | 2/1998 | Dewhurst et al. |
| 5,718,241 A | 2/1998 | Ben-Haim et al. |
| 5,718,701 A | 2/1998 | Shai et al. |
| 5,720,775 A | 2/1998 | Larnard |
| 5,722,401 A | 3/1998 | Pietroski et al. |
| 5,722,403 A | 3/1998 | McGee et al. |
| 5,722,963 A | 3/1998 | Lurie et al. |
| 5,725,494 A | 3/1998 | Brisken |
| 5,725,512 A | 3/1998 | Swartz et al. |
| 5,728,062 A | 3/1998 | Brisken |
| 5,730,127 A | 3/1998 | Avitall |
| 5,730,704 A | 3/1998 | Avitall |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,755,663 A | 5/1998 | Larsen et al. |
| 5,755,664 A | 5/1998 | Rubenstein |
| 5,755,715 A | 5/1998 | Stern et al. |
| 5,755,760 A | 5/1998 | Maguire et al. |
| 5,769,846 A | 6/1998 | Edwards et al. |
| 5,782,239 A | 7/1998 | Webster, Jr. |
| 5,782,898 A | 7/1998 | Dahl et al. |
| RE35,880 E | 8/1998 | Waldman et al. |
| 5,797,842 A | 8/1998 | Pumares et al. |
| 5,797,877 A | 8/1998 | Hamilton et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,429 A | 9/1998 | Edwards |
| 5,800,432 A | 9/1998 | Swanson |
| 5,807,249 A | 9/1998 | Qin et al. |
| 5,807,308 A | 9/1998 | Edwards |
| 5,807,391 A | 9/1998 | Wijkamp |
| 5,807,395 A | 9/1998 | Mulier et al. |
| 5,840,031 A | 11/1998 | Crowley |
| 5,840,076 A | 11/1998 | Swanson et al. |
| 5,842,984 A | 12/1998 | Avitall |
| 5,843,154 A | 12/1998 | Osypka |
| 5,846,218 A | 12/1998 | Brisken et al. |
| 5,885,278 A | 3/1999 | Fleischman |
| 5,921,982 A | 7/1999 | Lesh et al. |
| 5,938,660 A | 8/1999 | Swartz et al. |
| 5,971,983 A | 10/1999 | Lesh |
| 6,001,093 A | 12/1999 | Swanson et al. |
| 6,012,457 A | 1/2000 | Lesh |
| 6,024,740 A | 2/2000 | Lesh |
| 6,064,902 A | 5/2000 | Haissaguerre et al. |
| 6,071,279 A | 6/2000 | Whayne et al. |
| 6,071,281 A | 6/2000 | Burnside et al. |
| 6,071,282 A | 6/2000 | Fleischman |
| 6,090,084 A | 7/2000 | Hassett et al. |
| 6,117,101 A | 9/2000 | Diederich et al. |
| 6,146,379 A | 11/2000 | Fleischman et al. |
| 6,161,543 A | 12/2000 | Cox et al. |
| 6,214,002 B1 | 4/2001 | Fleischman et al. |
| 6,237,605 B1 | 5/2001 | Vaska et al. |
| 6,502,576 B1 * | 1/2003 | Lesh .................. 128/898 |

FOREIGN PATENT DOCUMENTS

| | | |
|---|---|---|
| DE | 195 37 084 A1 | 4/1997 |
| EP | 0 149 431 | 7/1985 |
| EP | 0 452 278 A2 | 10/1991 |
| EP | 0 452 278 B1 | 10/1991 |
| EP | 0 472 368 A2 | 2/1992 |
| EP | 0 609 182 A1 | 8/1994 |
| EP | 0 711 573 A1 | 11/1994 |
| EP | 0 672 431 A2 | 9/1995 |
| EP | 0 672 432 A1 | 9/1995 |
| WO | WO 93/00958 | 1/1993 |
| WO | WO 93/08755 | 5/1993 |
| WO | WO 93/16632 | 9/1993 |
| WO | WO 93/20767 | 10/1993 |
| WO | WO 93/20770 | 10/1993 |
| WO | WO 93/20886 | 10/1993 |
| WO | WO 94/00050 | 1/1994 |
| WO | WO 94/21165 | 9/1994 |
| WO | WO 94/21167 | 9/1994 |
| WO | WO 94/21168 | 9/1994 |
| WO | WO 95/05781 | 3/1995 |
| WO | WO 95/10318 | 4/1995 |
| WO | WO 95/10319 | 4/1995 |
| WO | WO 95/10321 | 4/1995 |
| WO | WO 95/15115 | 6/1995 |

| | | |
|---|---|---|
| WO | WO 95/19738 | 7/1995 |
| WO | WO 96/00036 | 1/1996 |
| WO | WO 96/10961 | 4/1996 |
| WO | WO 96/26675 | 9/1996 |
| WO | WO 96/32885 | 10/1996 |
| WO | WO 96/32897 | 10/1996 |
| WO | WO 97/32525 | 9/1997 |
| WO | WO 97/37607 | 10/1997 |
| WO | WO 97/45156 | 12/1997 |
| WO | WO 98/02201 | 1/1998 |
| WO | WO 98/49957 | 11/1998 |
| WO | WO 99/00064 | 1/1999 |

OTHER PUBLICATIONS

Diederich, C.J. et al.; "The Development of Intracavitary Ultrasonic Applicators for Hyperthermia: a Designa ND Experimental Study," MEd. Phys. vol. 17, No. 4, pp. 626-634, Jul./Aug., 1990.

Diederich, C.J. et al.; "Induction of Hyperthermia Using an Intracavitary Multielement Ultrasonic Applicator," IEEE Transactions on Biomedical Engineering, vol. 36, No. 4, pp. 432-438, Apr., 1989.

Cox, James L.; "The Surgical Treatment of Atrial Fibrillation," J. Thoracic Cardio Vasc. Surg., vol. 101, pp. 402-405, (1991).

Cox, James L.; "The Surgical Treatment of Atrial Fibrillation," J. Thorrac. CArdio. Surg., vol. 101, pp. 584-592, (1991).

Fram, Daniel B. et al.; "Feasibility of Radiofrequency Poweed, Thermal Balloon Ablation of Atrioventricular Bypass Tracts Via the Coronary Sinus: in Vivo Canine Studies," PACE, vol. 18, pp. 1518-1530, Aug., 1995.

Haissaguerre, Michel et al.; "Right and Left Atrial Radiofrequency Catheter Therapy of Paroxysmal Atrial Fibrillation," J. Cardiovasc Electrophysiol, vol. 7, pp. 1132-1144, Dec. 1996.

Hindricks, Gerhard et al.; "Catheter Ablation," Current Management of Arrhythmias, pp. 373-378.

Jais, Pierre, et al.; "A Focal Source of Atrial Fibrillation Treated by Discrete Radiofrequency Ablation," Circulation, vol. 95, No. 3, pp. 572-576, Feb. 4, 1997.

Lesh, Michael D.; "Interventional Electrophysiology-State of the Art 1993," American Heart Journal, vol. 126, No. 3, Part 1, pp. 686-698, Sep. 1993.

Jais, Pierre et al.; "Biatrial Dimensions Relevant to Catheter Ablation," 17th Annual Scientific Sessions Abstract Form, pp. 1, Dec. 1, 1995.

McMath, Linda P. et al.; "Percutaneous Laser Balloon Coagulation of Accessory Pathways," SPIE, vol. 1425, Diagnostic and Therapeutic Cardiovascular Interventions, pp. 165-171, (1991).

Schuger, Claudio D. et al.; "Long-Term Effects of Percutaneous Laser Balloon Ablation From the Canine Coronary Sinus," Circulation, vol. 86, pp. 947-954, Sep. 1992.

Sueda, Taijiro et al.; "Simple Left Atrial Procedure for Chronic Atrial Fibrillaiton Associated with Mitral Valve Disease," Ann. Thorac. Surg., vol. 62, pp. 1796-1800, (1996).

* cited by examiner

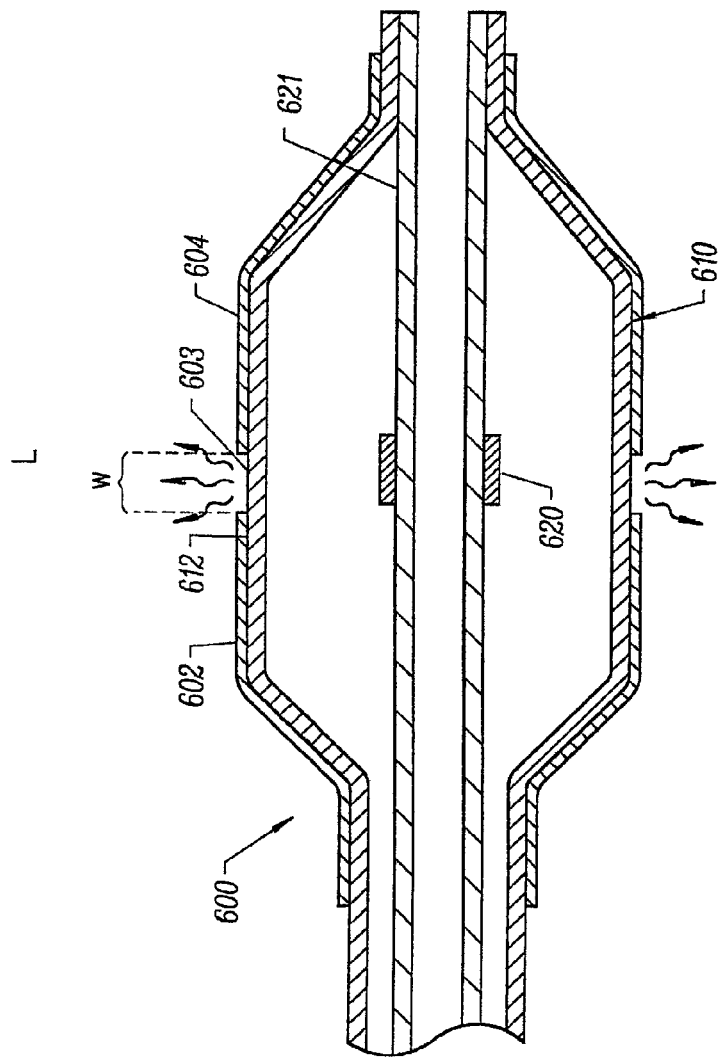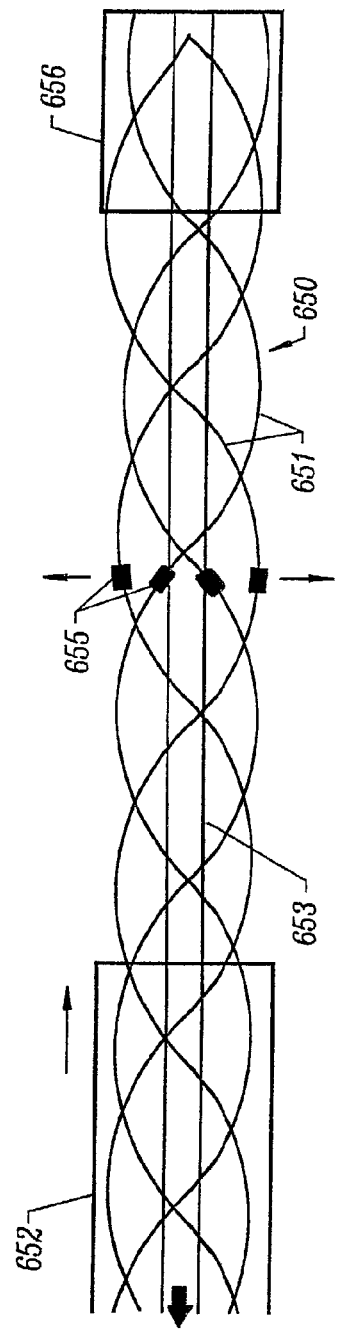
FIG. 13
FIG. 14

DEVICE AND METHOD FOR FORMING A CIRCUMFERENTIAL CONDUCTION BLOCK IN A PULMONARY VEIN

CROSS-REFERENCE TO RELATED APPLICATIONS

This application is a continuation of application Ser. No. 09/642,251 filed on Aug. 17, 2000, now U.S. Pat. No. 6,502,576 incorporated herein by reference, which is a continuation of application Ser. No. 09/384,727 filed on Aug. 27, 1999, now U.S. Pat. No. 6,305,378, incorporated herein by reference, which is a continuation of application Ser. No. 08/889,835 filed on Jul. 8, 1997, now U.S. Pat. No. 6,012,457, incorporated herein by reference. This application is also a continuation-in-part of application Ser. No. 09/357,184 filed on Jul. 19, 1999, now U.S. Pat. No. 6,471,697, incorporated herein by reference, which is a continuation of application Ser. No. 08/853,861 filed on May 9, 1997, now U.S. Pat. No. 5,971,983, incorporated herein by reference.

TECHNICAL FIELD

The present invention is a surgical method. More specifically, it is a method for treating atrial fibrillation by creating a circumferential conduction block in a pulmonary vein wall. Still more specifically, it is a method for ablating a selected circumferential region of tissue along a pulmonary vein wall which transects the electrical conductivity of the pulmonary vein relative to its longitudinal axis.

BACKGROUND

Atrial Fibrillation

Cardiac arrhythmias, and atrial fibrillation in particular, persist as common and dangerous medical ailments, especially in the aging population. In patients with normal sinus rhythm, the heart, which is comprised of atrial ventricular, and excitatory conduction tissue, is electrically excited to beat in a synchronous, patterned fashion. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been generally known to occur at various regions of the heart, and particularly in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as for example in U.S. Pat. No. 4,641,649 to Walinsly et al. and WO 96/32897 to Desai.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Conventional Atrial Arrhythmia Treatments

Several pharmacological approaches intended to remedy or otherwise treat atrial arrhythmias have been disclosed, such as, for example, in U.S. Pat. No. 4,673,563 to Berne et al.; U.S. Pat. No. 4,569,801 to Molloy et al.; and also by Hindricks, et al. in "Current Management of Arrhythmias" (1991). However, such pharmacological solutions are not generally believed to be entirely effective in many cases, and may in some cases result in proarrhythmia and long term inefficacy.

Several surgical approaches have also been developed with the intention of treating atrial fibrillation. One particular example is known as the "maze procedure," as is disclosed by Cox, J L et al. in "The surgical treatment of atrial fibrillation. I. Summary" *Thoracic and Cardiovascular Surgery* 101(3), pp. 402–405 (1991); and also by Cox, J L in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

While the "maze" procedure as reported by Cox and others, and also other surgical procedures, have met some success in treating patients with atrial arrhythmia, its highly invasive methodology is believed to be prohibitive in most cases. However, these procedures have provided a guiding principle that mechanically isolating faulty cardiac tissue may successfully prevent atrial arrhythmia, and particularly atrial fibrillation caused by perpetually wandering reentrant wavelets or focal regions of arrhythmogenic conduction.

Modern Catheter Treatments

Success with surgical interventions through atrial segmentation, particularly with regard to the surgical "maze" procedure just described, has inspired the development of less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as are disclosed in the following U.S. patents: U.S. Pat. No. 5,617,854 to Munsif; U.S. Pat. No. 4,898,591 to Jang et al.; U.S. Pat. No. 5,487,385 to Avitall; and U.S. Pat. No. 5,582,609 to Swanson. The disclosures of these patents are herein incorporated in their entirety by reference thereto.

Additional examples of catheter-based tissue ablation in performing less-invasive cardiac chamber segmentation procedures are also disclosed in the following articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132–1144 (1996). These articles are herein incorporated in their entirety by reference thereto.

Furthermore, the use of particular guiding sheath designs for use in ablation procedures in both the right and/or left atrial chambers are disclosed in U.S. Pat. Nos. 5,427,119; 5,497,119; 5,564,440; 5,575,766 to Swartz et al. In addition, various energy delivery modalities have been disclosed for forming such atrial wall lesions, and include use of microwave, laser, and more commonly, radiofrequency energies to create conduction blocks along the cardiac tissue wall, as disclosed in WO 93/20767 to Stern et al.; U.S. Pat. No. 5,104,393 to Isner et al.; and U.S. Pat. No. 5,575,766 to Swartz et al, respectively. The disclosures of these references are herein incorporated in their entirety by reference thereto.

In addition to attempting atrial wall segmentation with long linear lesions for treating atrial arrhythmia, ablation catheter devices and methods have also been disclosed which are intended to ablate arrhythmogenic tissue of the left-sided accessory pathways, such as those associated with the Wolff-Parkinson-White syndrome, through the wall of an adjacent region along the coronary sinus.

For example, Fram et al., in "Feasibility of RF Powered Thermal Balloon Ablation of Atrioventricular Bypass Tracts via the Coronary Sinus: In vivo Canine Studies," *PACE*, Vol. 18, p 1518–1530 (1995), disclose attempted thermal ablation of left-sided accessory pathways in dogs using a balloon which is heated with bipolar radiofrequency electrodes positioned within the balloon. A 10 French guiding catheter and a 0.035" wire were provided in an assembly adapted to advance the ablation catheter into the coronary sinus from the jugular vein. Thermal ablation procedures were performed in the posterospetal coronary sinus and in the left free-wall coronary sinus with thermal inflations at either 70 deg, 80 deg, or 90 deg for either 30 or 60 seconds. In all cases balloon occlusion was confirmed using distal dye injection. A compliant silicone balloon was used which had a diameter range of 5–20 mm and a length range of 8–23 mm over a final inflation pressure range of 0.4 to 1.5 atms. Fram et al. discloses that the lesion depth of some population groups may be sufficient to treat patients with Wolff-Parkinson-White syndrome.

Additional examples of cardiac tissue ablation from the region of the coronary sinus for the purpose of treating particular types of cardiac arrhythmias are disclosed in: "Long-term effects of percutaneous laser balloon ablation from the canine coronary sinus", Schuger C D et al., *Circulation* (1992) 86:947–954; and "Percutaneous laser balloon coagulation of accessory pathways", McMath L P et al., Diagn Ther Cardiovasc Interven 1991; 1425:165–171.

Focal Arrhythmias Originating from Pulmonary Veins

Atrial fibrillation may be focal in nature, caused by the rapid and repetitive firing of an isolated center within the atrial cardiac muscle tissue. These foci, defined by regions exhibiting a consistent and centrifugal pattern of electrical activation, may act as either a trigger of atrial fibrillatory paroxysmal or may even sustain the fibrillation. Recent studies have suggested that focal arrhythmia often originates from a tissue region along the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways.

One example of a focal ablation method intended to destroy and thereby treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132–1144 (1996). Haissaguerre, et al. disclose radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and were ablated using a standard 4 mm tip single ablation electrode.

In another focal ablation example, Jais et al. in "A focal source of atrial fibrillation treated by discrete radiofrequency ablation" *Circulation* 95:572–576 (1997) applies an ablative technique to patients with paroxysmal arrhythmias originating from a focal source. At the site of arrhythmogenic tissue, in both right and left atria, several pulses of a discrete source of radiofrequency energy were applied in order to eliminate the fibrillatory process.

None of the cited references discloses a method for treating left atrial fibrillation by transecting the electrical conductivity of a pulmonary vein to thereby block arrhythmogenic conduction along the longitudinal axis of the vein and into the left atrial wall.

Nor do the cited references disclose creating a circumferential conduction block along a circumferential path of tissue along the pulmonary vein wall which circumscribes the pulmonary vein lumen.

Nor do the cited references disclose forming such a circumferential conduction block with a circumferential ablation device assembly in a percutaneous translumenal procedure wherein an ablation element on an elongate catheter body is introduced into a pulmonary vein and is actuated to ablate a circumferential lesion in the pulmonary vein wall in order to form the circumferential conduction block.

Nor do the cited references disclose creating a circumferential conduction block along a circumferential path of tissue in a pulmonary vein wall which circumscribes the pulmonary vein lumen and which intersects with one or more long linear lesions which include at least in part a region of the pulmonary vein ostium.

SUMMARY OF THE INVENTION

The present invention is a method for treating atrial arrhythmias by forming a circumferential conduction block along a circumferential path of tissue in a pulmonary vein wall which circumscribes the pulmonary vein lumen and transects the electrical conductivity of the pulmonary vein relative to its longitudinal axis. One aspect of the method includes diagnosing a patient with atrial arrhythmia originating from at least one left pulmonary vein and then treating the arrhythmia by forming a circumferential conduction block along the pulmonary vein wall that either includes the focal origin or is located between the focus and the left atrial wall. Another aspect of the method includes diagnosing a patient with multiple wavelet type arrhythmias and then treating the arrhythmia by forming the circumferential conduction block such that it intersects with two linear lesions each formed between the pulmonary vein and two other, adjacent pulmonary veins in a less-invasive "maze" type of procedure.

A further variation of the inventive method includes forming the circumferential conduction block with a circumferential ablation device assembly that includes a circumferential ablation element located on the distal end portion of an elongate catheter body. The method according to this variation includes: positioning the circumferential ablation element within the pulmonary vein at a circumferential ablation region along the longitudinal axis of the pulmonary vein wall where the circumferential conduction block is to be desirably formed; and actuating the circumferential ablation element with an ablation actuator to form a circumferential lesion by ablating a circumferential path of tissue along a circumference of the pulmonary vein wall that circumscribes the pulmonary vein lumen. In a further aspect of this variation, the circumferential ablation element includes an expandable member with a working length which is adjusted from a radially collapsed position to a radially expanded position in order to engage the ablation element with the inner lining of the pulmonary vein. In yet another aspect of this variation, the circumferential ablation element is used to form the circumferential lesion such that the lesion length relative to the longitudinal axis of the pulmonary vein is shorter than the lesion circumference which circumscribes the pulmonary vein lumen.

A further variation of the invention includes monitoring the electrical conduction signals along the pulmonary vein wall with a signal monitoring circuit; and then identifying an origin of left atrial arrhythmia in the pulmonary vein based upon the monitored electrical conduction signals.

Another further variation of the invention includes providing a test, stimulus on one side of the circumferential conduction block after it has been formed and then monitoring the electrical conduction on the other side of the conduction block.

Another variation of the invention includes forming a circumferential conduction block at an ablation region along a circumference of a pulmonary vein wall which circumscribes the pulmonary vein lumen and which intersects with at least two linear lesions in a less-invasive "maze"-type method for forming a "boxed" conduction block around a region of the left atrial wall defined in part by the pulmonary vein ostia.

BRIEF DESCRIPTION OF THE DRAWINGS

FIGS. 8A–B show perspective views of another circumferential ablation catheter variation during use in a left atrium according to the method of FIG. 3, wherein FIG. 8A shows a radially compliant expandable member with a working length adjusted to a radially expanded position while in the left atrium, and FIG. 8B shows the expandable member after advancing it into and engaging a pulmonary vein ostium while in the radially expanded position.

FIG. 13 shows a cross-sectional view of another circumferential ablation member for use in the method of FIG. 3, wherein the circumferential ablation element circumscribes an outer surface of an expandable member substantially along its working length and is insulated at both the proximal and the distal ends of the working length to thereby form an uninsulated equatorial or otherwise circumferential band in a region of the working length which is adapted to ablate tissue.

FIG. 14 shows a perspective view of another circumferential ablation member which is adapted for use in the method of the present invention, wherein the expandable member is shown to be a cage of coordinating wires which are adapted to be adjusted from a radially collapsed position to a radially expanded position in order to engage electrode elements on the wires in a circumferential pattern about a pulmonary vein wall.

DETAILED DESCRIPTION OF THE EMBODIMENTS

Figure 1:
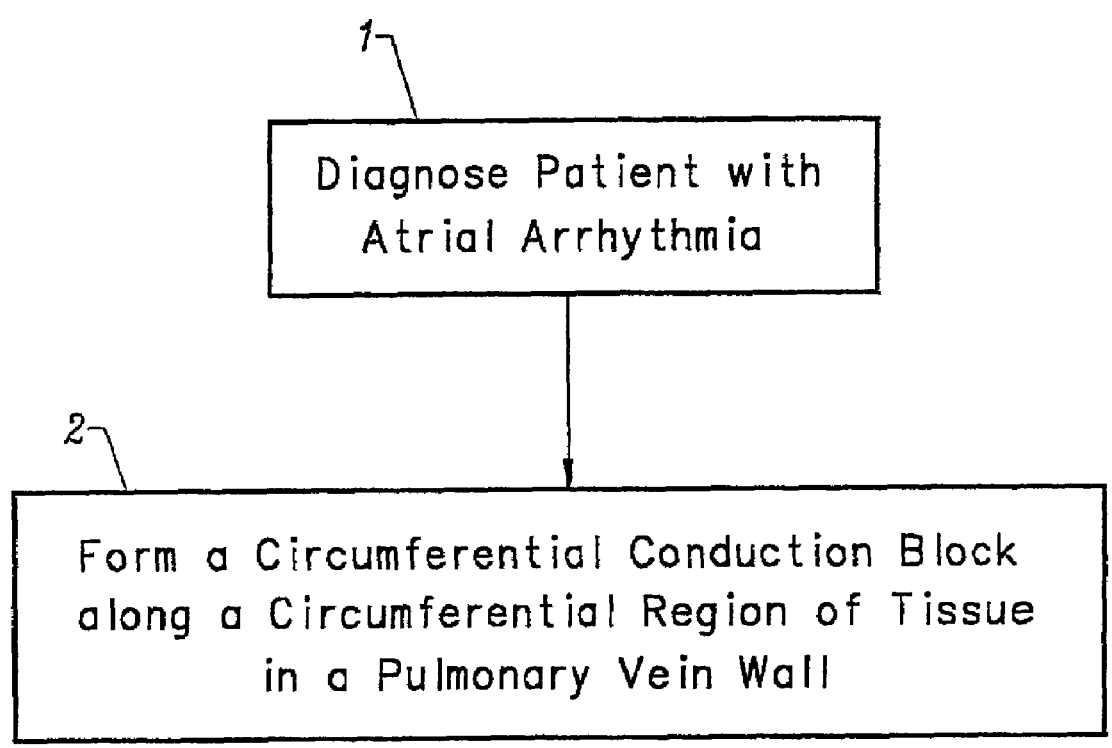
FIG. 1 diagrammatically shows sequential, general steps for treating atrial arrhythmia according to the method of the present invention.

As diagrammatically illustrated in the flow diagram of FIG. 1, the present invention is a method for treating patients diagnosed with atrial arrhythmia by forming a circumferential conduction block in a pulmonary vein which blocks electrical conduction along the longitudinal axis of the pulmonary vein wall and into the left atrium.

The terms "circumference" or "circumferential", including derivatives thereof, are herein intended to mean a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, is herein intended to mean to enclose, surround, or encompass a defined region of space. Therefore, according to these defined terms, a continuous line which is traced around a region of space and which starts and ends at the same location "circumscribes" the region of space and has a "circumference" which is defined by the distance the line travels as it translates along the path circumscribing the space.

Still further, a circumferential path or element may include one or more of several shapes, and may be for example circular, oblong, ovular, elliptical, or otherwise planar enclosures. A circumferential path may also be three dimensional, such as for example two opposite-facing semi-circular paths in two different parallel or off-axis planes which are connected at their ends by line segments bridging between the planes.

Figure 2A:
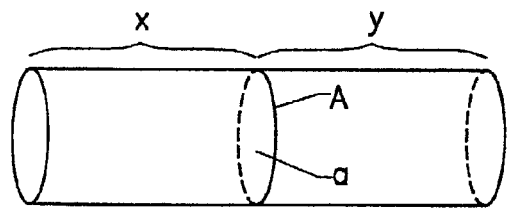
FIGS. 2A–E show schematic, perspective views of various circumferential conduction blocks formed in pulmonary vein wall tissue according to the method of FIG. 1.
Figure 2B:
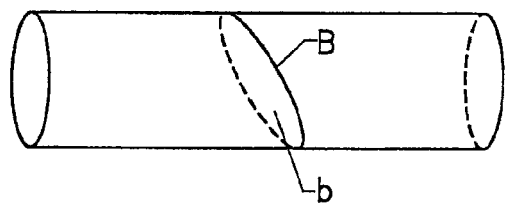
Figure 2C:
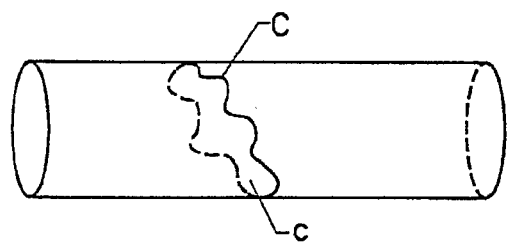
Figure 2D:
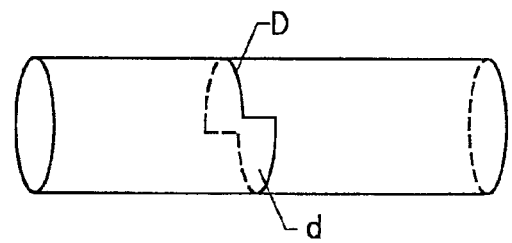
Figure 2E:
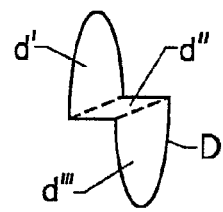

For purpose of further illustration, FIGS. 2A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 2D, FIG. 2E shows an exploded perspective view of circumferential path D as it circumscribes multiplanar portions of the pulmonary vein lumen shown at d', d", and d'", which together make up region d as shown in FIG. 1D.

The term "transect", including derivatives thereof, is also herein intended to mean to divide or separate a region of space into isolated regions. Thus, each of the regions circumscribed by the circumferential paths shown in FIGS. 2A–D transects the respective pulmonary vein, including its lumen and its wall, to the extent that the respective pulmonary vein is divided into a first longitudinal region located on one side of the transecting region, shown for example at region "X" in FIG. 2A, and a second longitudinal region on the other side of the transecting plane, shown for example at region "Y" also in FIG. 2A.

Therefore, a "circumferential conduction block" according to the present invention is formed along a region of tissue which follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue.

The term "element" within the context of "ablation element" is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryoblation element adapted to sufficiently cool tissue to substantially alter the structure thereof may be suitable if adapted according to the teachings of the current invention. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that tissue.

The term "diagnose", including derivatives thereof, is intended to include patients suspected or predicted to have atrial arrhythmia, in addition to those having specific symptoms or mapped electrical conduction indicative of atrial arrhythmia.

Returning to the inventive method as shown in FIG. 1, a patient diagnosed with atrial arrhythmia according to diagnosing step (1) is treated with a circumferential conduction block according to treatment step (2). In one aspect, a patient diagnosed according to diagnosis step (1) with multiple wavelet arrhythmia originating from multiple regions along the atrial wall may also be treated in part by forming the circumferential conduction block according to treatment step (2), although as an adjunct to forming long linear regions of conduction block between adjacent pulmonary vein ostia in a less-invasive "maze"-type catheter ablation procedure. More detail regarding this particular aspect of the inventive method is provided below with reference to a combination circumferential-long linear lesion ablation device which is described below with reference to FIGS. 9A–E.

In another aspect of the method of FIG. 1, a patient diagnosed with focal arrhythmia originating from an arrhythmogenic origin or focus in a pulmonary vein is treated according to this method when the circumferential conduction block is formed along a circumferential path of wall tissue that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening circumferential conduction block.

In still a further aspect of the method shown in FIG. 1, the circumferential conduction block may be formed in one of several ways according to treatment step (2). In one example not shown, the circumferential conduction block may be formed by a surgical incision or other method to mechanically transect the pulmonary vein, followed by suturing the transected vein back together. As the circumferential injury is naturally repaired, such as through a physiologic scarring response common to the "maze" procedure, electrical conduction will generally not be restored across the injury site. In another example not shown, a circumferential conduction block of one or more pulmonary veins may be performed in an epicardial ablation procedure, wherein an ablation element is either placed around the target pulmonary vein or is translated circumferentially around it while being energized to ablate the adjacent tissue in an "outside-in" approach. This alternative method may be performed during an open chest-type procedure, or may be done using other known epicardial access techniques.

Notwithstanding the alternative methods just described for forming the circumferential conduction block according to treatment step (2) of FIG. 1, FIGS. 3–12 collectively show variations of methods and related device assemblies according to one preferred illustrative embodiment which uses a circumferential ablation device assembly for forming a circumferential conduction block in a percutaneous translumenal circumferential ablation procedure.

Figure 3:
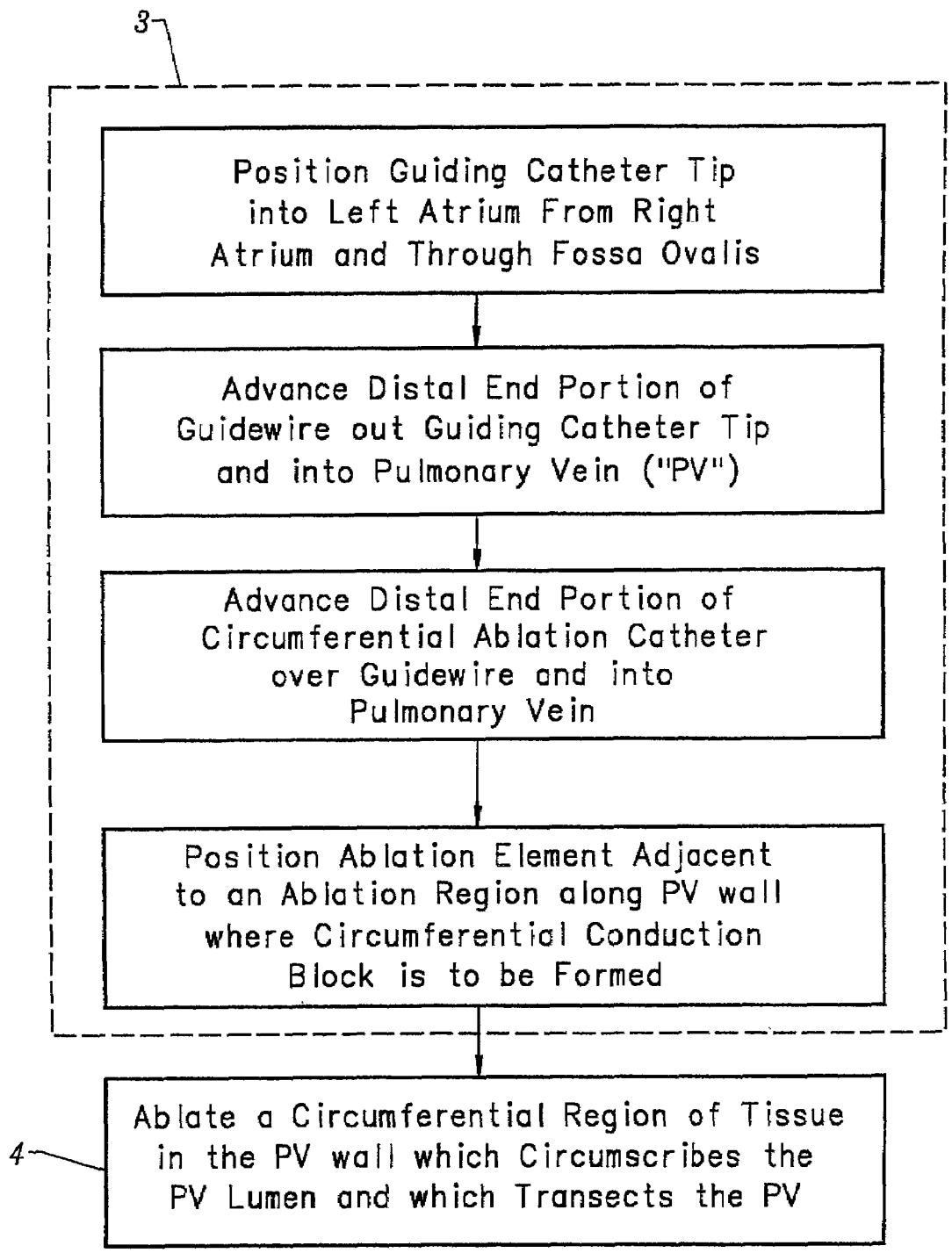
FIG. 3 shows a flow diagram of sequential steps for performing the method of the present invention according to an illustrative percutaneous translumenal catheter embodiment which uses a circumferential ablation device assembly.

FIG. 3 diagrammatically shows the sequential steps of a detailed circumferential ablation method for forming a circumferential conduction block in a pulmonary vein as one variation for performing treatment step (2) of FIG. 1. The circumferential ablation method according to FIG. 3 includes: positioning a circumferential ablation element at an ablation region along the pulmonary vein according to a series of detailed steps shown collectively in FIG. 3 as positioning step (3); and thereafter ablating a continuous circumferential region of tissue in the PV wall at the ablation region according to ablation step (4).

Further to positioning step (3) according to the method of FIG. 3, a distal tip of a guiding catheter is first positioned within the left atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brochenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

It is however further contemplated that other left atrial access methods may be suitable substitutes in the novel arrhythmia treatment method of the present invention. In one alternative variation not shown, a "retrograde" approach may be used, wherein the guiding catheter is advanced into the left atrium from the arterial system. In this variation, the. Seldinger technique is employed to gain vascular access into the arterial system, rather than the venous, for example at a femoral artery. The guiding catheter is advanced retrogradedly through the aorta, around the aortic arch, into the ventricle, and then into the left atrium through the mitral valve.

Subsequent to gaining transeptal access to the left atrium as just described, positioning step (3). according to FIG. 3 next includes advancing a guidewire into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) which is coaxial within the guiding catheter, such as for example by using one of the directional catheters disclosed in U.S. Pat. No. 5,575,766 to Swartz. Or, the guidewire may have sufficient stiffness and maneuverability in the left atrial cavity to unitarily subselect the desired pulmonary vein distally of the guiding catheter seated at the fossa ovalis.

Suitable guidewire designs for use according to the illustrative catheter ablation method may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010" to 0.035" may be suitable. In cases where the guidewire is used to bridge the atrium from the guiding catheter at the fossa ovalis, and where no other sub-selective guiding catheters are used, guidewires having an outer diameter ranging from 0.018" to 0.035" may be required. It is believed that guidewires within this size range may be required to provide sufficient stiffness and maneuverability in order to allow for guidewire control and to prevent undesirable guidewire prolapsing within the relatively open atrial cavity.

Subsequent to gaining pulmonary vein access, positioning step (3) of FIG. 3 next includes tracking the distal end portion of a circumferential ablation device assembly over the guidewire and into the pulmonary vein, followed by positioning an ablation element at an ablation region of the pulmonary vein where the circumferential conduction block is to be desirably formed.

Figure 4:
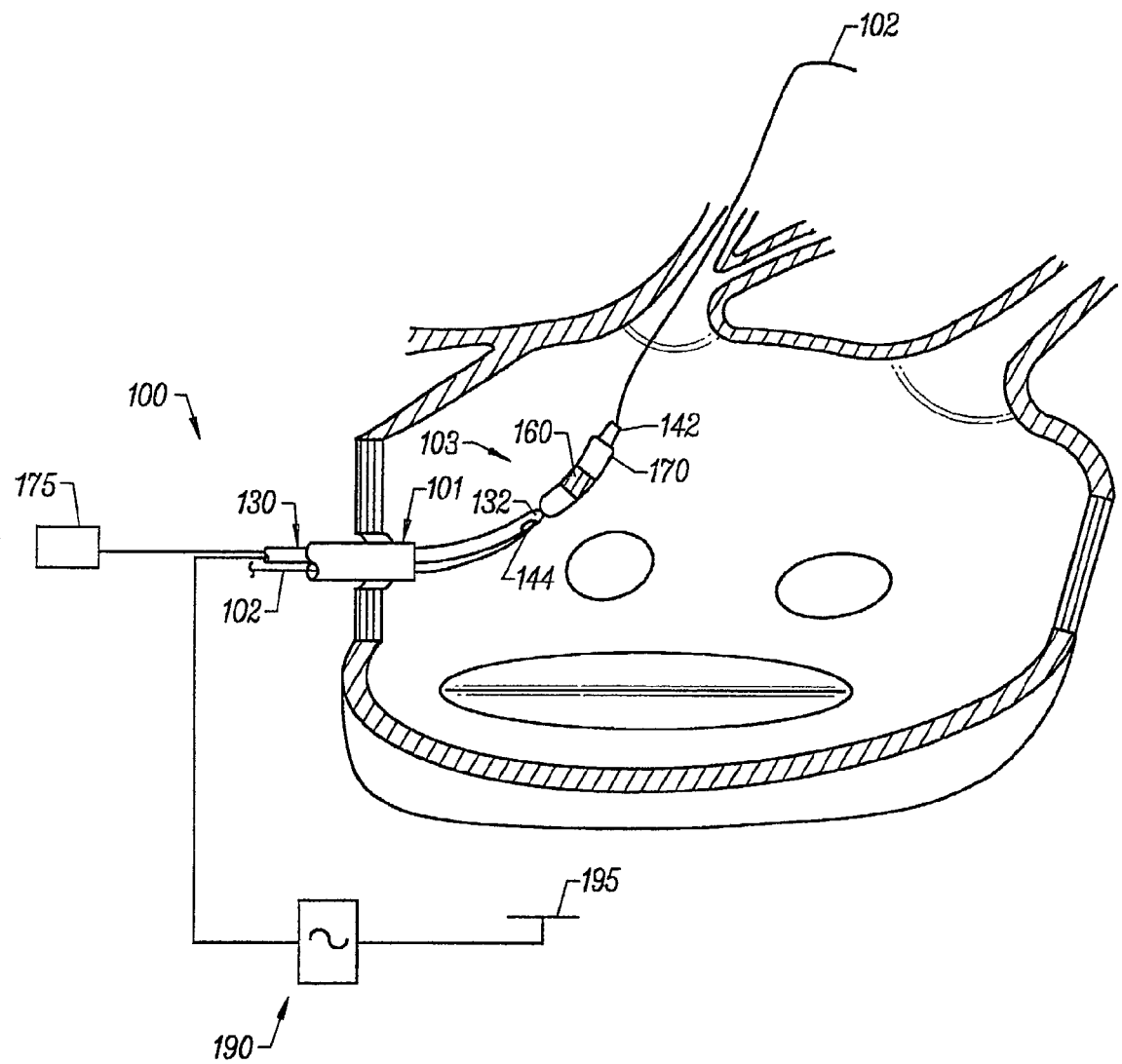
FIG. 4 shows a perspective view of a circumferential ablation device assembly during use in a left atrium subsequent to performing transeptal access and guidewire positioning steps according to the method of FIG. 3.
Figure 5:
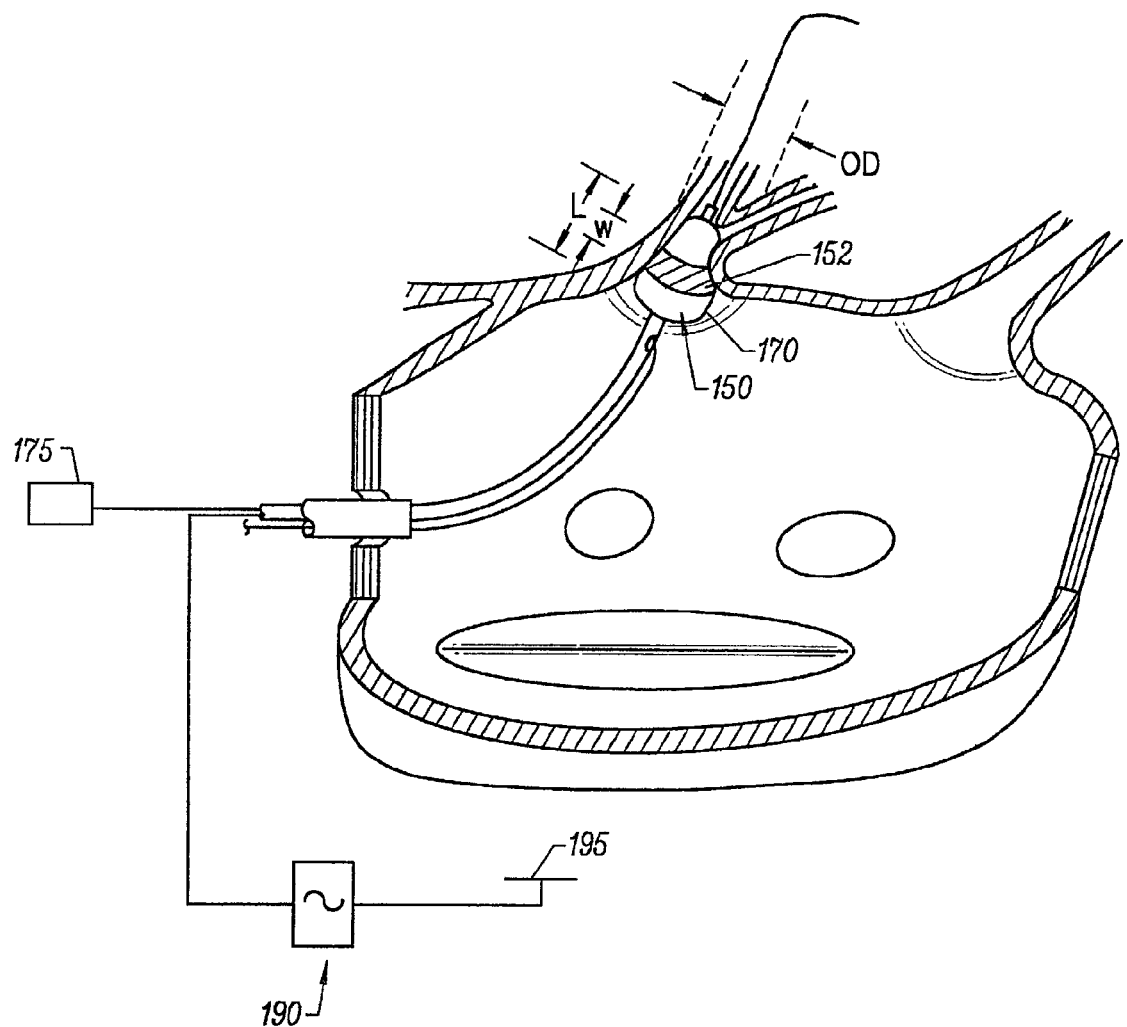
FIG. 5 shows a similar perspective view of the circumferential ablation device assembly shown in FIG. 4, and further shows a circumferential ablation catheter during use in ablating a circumferential region of tissue along a pulmonary vein wall to form a circumferential conduction block in the pulmonary vein according to the method of FIG. 3.

FIGS. 4–5 further show a circumferential ablation device assembly (100) during use in performing positioning step (3) and ablation step (4) just described with reference to FIG. 3. Included in the circumferential ablation device assembly (100) are guiding catheter (101), guidewire (102), and circumferential ablation catheter (103).

More specifically, FIG. 4 shows guiding catheter (101) subsequent to performing a transeptal access method according to FIG. 3, and also shows guidewire (102) subsequent to advancement and positioning within a pulmonary vein, also according to step (3) of FIG. 3. FIG. 4 shows circumferential ablation catheter (103) as it tracks coaxially over guidewire (102) with a distal guidewire tracking member, which is specifically shown only in part at first and second distal guidewire ports (142,144) located on the distal end portion (132) of an elongate catheter body (130). A guidewire lumen (not shown) extends between the first and second distal guidewire ports (142,144) and is adapted to slideably receive and track over the guidewire. In the particular variation of FIG. 4, the second distal guidewire port (144) is located on a distal end portion (132) of the elongate catheter body (130), although proximally of first distal guidewire port (142).

As would be apparent to one of ordinary skill, the distal guidewire tracking member shown in FIG. 4 and just described may be slideably coupled to the guidewire externally of the body in a "backloading" technique after the guidewire is first positioned in the pulmonary vein. Furthermore, there is no need in this variation for a guidewire lumen in the proximal portions of the elongate catheter body (130), which allows for a reduction in the outer diameter of the catheter shaft in that region. Nevertheless, it is further contemplated that a design which places the second distal guidewire port on the proximal end portion of the elongate catheter body would also be acceptable, as is described below for example with reference to the perfusion embodiment of FIGS. 6A–6B.

In addition, the inclusion of a guidewire lumen extending within the elongate body between first and second ports, as provided in FIG. 4, should not limit the scope of acceptable guidewire tracking members according to the present invention. Other guidewire tracking members which form a bore adapted to slideably receive and track over a guidewire are also considered acceptable, such as for example the structure adapted to engage a guidewire as described in U.S. Pat. No. 5,505,702 to Arney, the entirety of which is hereby incorporated by reference herein.

While the assemblies and methods shown variously throughout the Figures include a guidewire coupled to a guidewire tracking member on the circumferential ablation catheter, other detailed variations may also be suitable for positioning the circumferential ablation element at the ablation region in order to form a circumferential conduction block there. For example, an alternative circumferential ablation catheter not shown may include a "fixed-wire"-type of design wherein a guidewire is integrated into the ablation catheter as one unit. In another alternative assembly, the same type of sub-selective sheaths described above with reference to U.S. Pat. No. 5,575,766 to Swartz for advancing a guidewire into a pulmonary vein may also be used for advancing a circumferential ablation catheter device across the atrium and into a pulmonary vein.

The method of ablating a circumferential lesion according to the present invention, such as according to the method of FIG. 3, may further include the expansion of an expandable member in order to circumferentially engage an inner lining of a pulmonary vein wall with a circumferential ablation element FIG. 4 therefore shows circumferential ablation catheter (103) with a circumferential ablation element (160) coupled to an expandable member (170). The expandable member (170) is shown in FIG. 4 in a radially collapsed position adapted for percutaneous translumenal delivery into the pulmonary vein according to positioning step (3) of FIG. 3.

However, expandable member (170) is also adjustable to a radially expanded position when actuated by an expansion actuator (175), as shown in FIG. 5. Expansion actuator (175) may include, but is not limited to, a pressurizeable fluid source. According to the expanded state shown in FIG. 5, expandable member (170) includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

Circumferential ablation element (160) also includes a circumferential band (152) on the outer surface of working length L which is coupled to an ablation actuator (190) at a proximal end portion of the elongate catheter body (shown schematically). After expandable member (170) is adjusted to the radially expanded position and at least a portion of working length L circumferentially engages the pulmonary vein wall in the ablation region, circumferential ablation element (160) is actuated by ablation actuator (190) to ablate the surrounding circumferential path of tissue in the pulmonary vein wall, thereby forming a circumferential lesion that circumscribes the pulmonary vein lumen and transects the electrical conductivity of the pulmonary vein to block conduction in a direction parallel to its longitudinal axis, i.e., in an axial direction along the pulmonary vein wall.

Figure 6B:
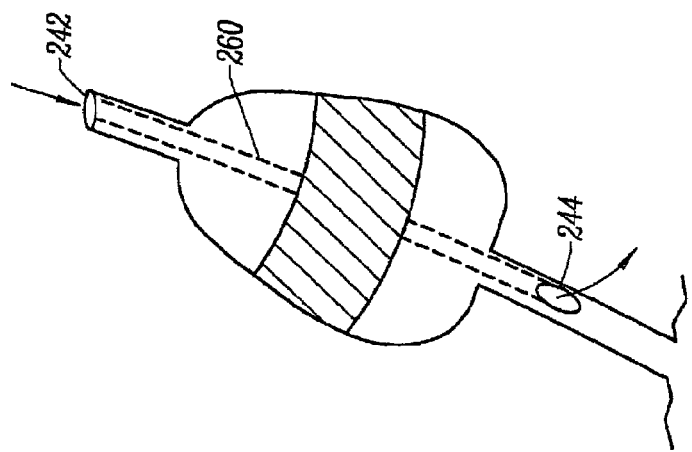
FIG. 6B is an enlarged partial view of the circumferential ablation catheter shown in FIG. 6A, with a perfusion lumen shown in phantom.
Figure 6A:
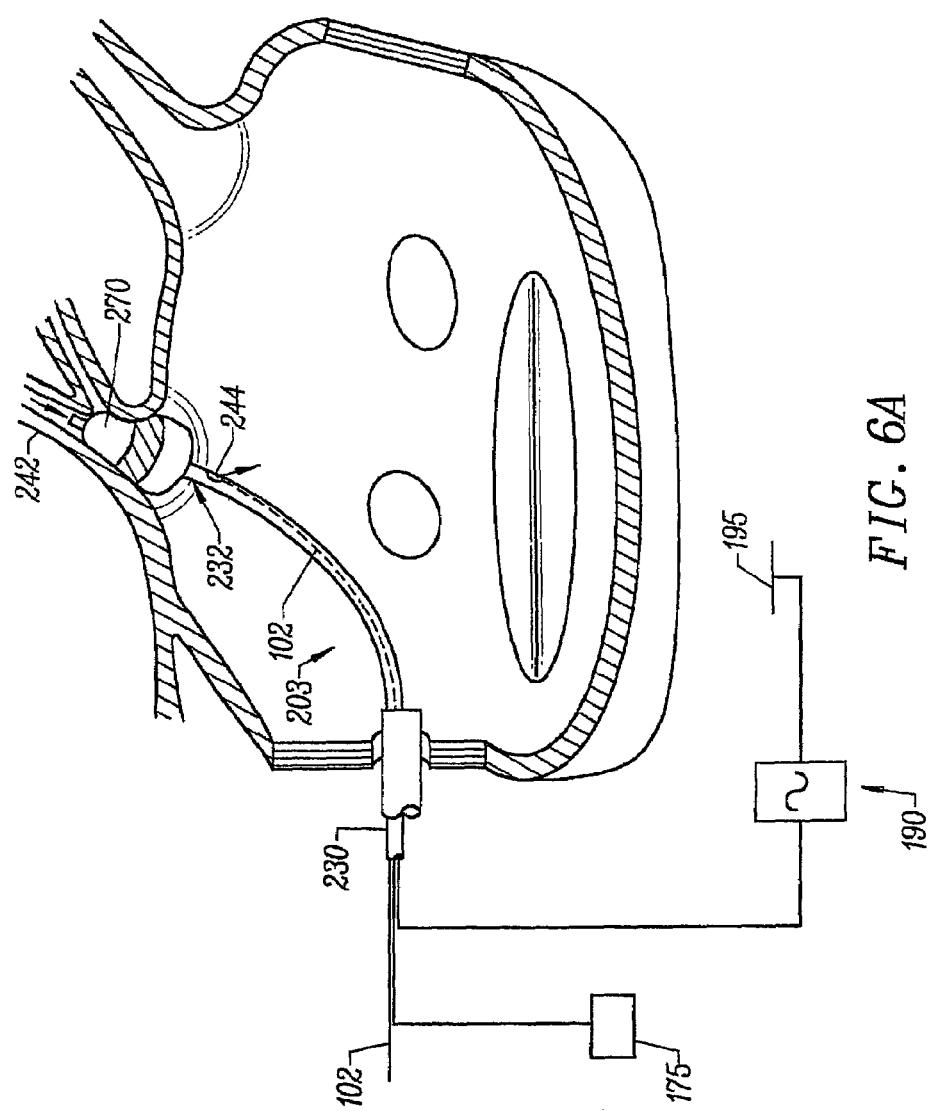
FIG. 6A shows a similar perspective view as shown in FIG. 5, although showing a further circumferential ablation catheter variation which is adapted to allow for blood perfusion from the pulmonary vein and into the atrium while performing the circumferential ablation method shown diagrammatically in FIG. 3.

FIG. 6A shows another circumferential ablation catheter (203) during use according to a further variation of the method of FIG. 3, wherein a perfusion lumen (260) (shown in phantom in FIG. 6B) is formed within the distal end portion (232) of elongate catheter body (230). The perfusion lumen (260) in this example is formed between a distal perfusion port, which in this example is the first distal guidewire port (242), and proximal perfusion port (244). Proximal perfusion port (244) is formed through the wall of the elongate catheter body (230) and communicates with the guidewire lumen (260) which also forms the perfusion lumen between the distal and proximal perfusion ports. In the particular design shown, after the guidewire has provided for the placement of the ablation element into the pulmonary vein, the guidewire is withdrawn proximally of the proximal perfusion port (244) (shown schematically in shadow) so that the lumen between the ports is clear for antegrade blood flow into the distal perfusion port (242), proximally along the perfusion lumen (260), out the proximal perfusion port (244) and into the atrium (perfusion flow shown schematically with arrows).

Further to the perfusion design and method of use shown in FIG. 6A, guidewire (102) is positioned in a guidewire lumen which extends the entire length of the elongate catheter body. (230) in an "over-the-wire"-type of design, which facilitates the proximal withdrawal of the guidewire to allow for perfusion while maintaining the ability to subsequently readvance the guidewire distally through the first distal guidewire port (242) for catheter repositioning. It is further contemplated that a "monorail"-type design such as that shown in the previous FIGS. 4–5 may also be acceptable for use in alternative perfusion variations. In one alternative variation not shown, the guidewire is simply withdrawn and disengaged from the second distal guidewire port (244), in which case the circumferential ablation catheter must generally be withdrawn from the body in order to recouple the distal guidewire tracking member with the guidewire. In another alternative perfusion variation, a proximal perfusion port is provided as a separate and distinct port positioned between the second distal guidewire port (244) and the expandable member (270), which allows for proximal withdrawal of the guidewire to clear the guidewire lumen and thereby form a perfusion lumen between the first distal guidewire port and the proximal perfusion port. The guidewire of this alternative variation, however, remains engaged within the guidewire lumen between the second distal guidewire port and the proximal perfusion port.

Passive perfusion during expansion of the expandable member is believed to minimize stasis and allow the target pulmonary vein to continue in its atrial filling function during the atrial arrhythmia treatment procedure. Without this perfusion feature, the method steps of expanding the expandable member to engage the vessel wall and thereafter ablating the circumferential lesion around the circumferential ablation element may result in undesirably thrombogenic flow stasis in the pulmonary vein distally to the expandable member. In addition, in cases where the ablation element chosen provides for heat generation at the ablation region, as described in more detail later, perfusion may also provide a cooling function. Moreover, in addition to the specific perfusion structure and related method of the FIG. 4 embodiment, it is to be further understood that other structural variants which allow for perfusion flow during expansion of the expandable element may function as suitable substitutes without departing from the scope of the present invention.

Figure 7:
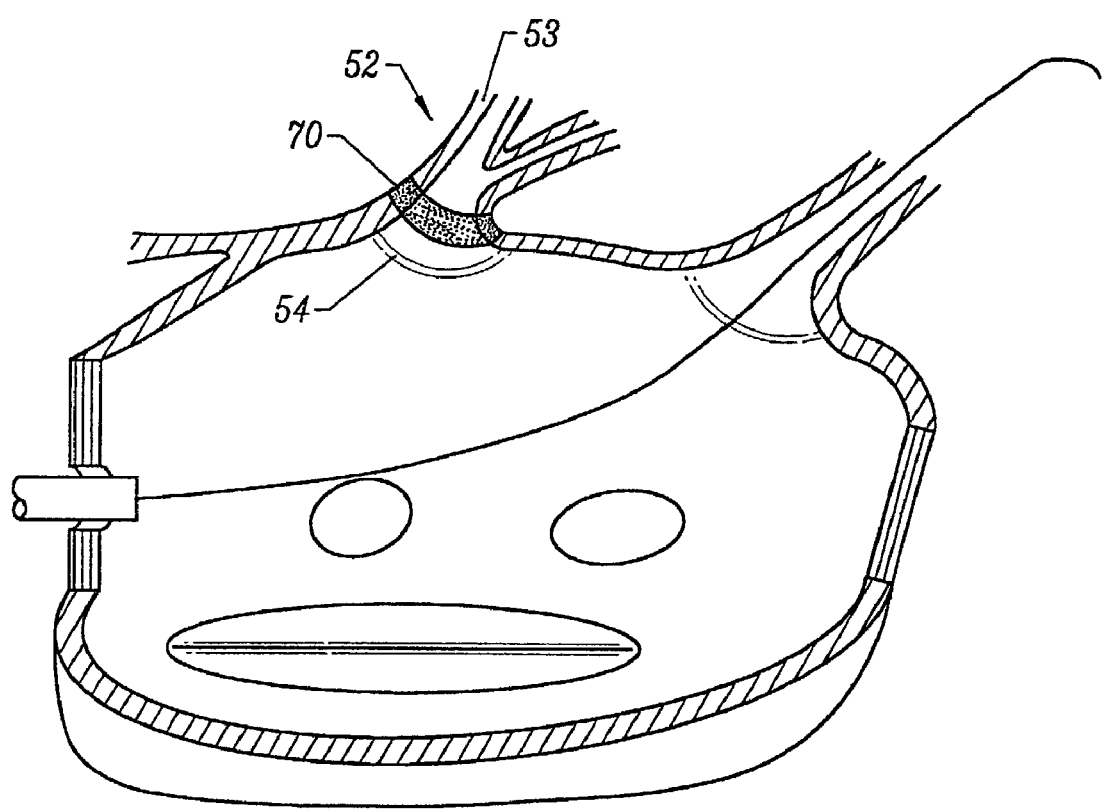
FIG. 7 shows a similar perspective view of the left atrium as that shown in FIGS. 4–6, although showing a cross-sectional view of a circumferential lesion after being formed by circumferential catheter ablation according to the method of FIG. 3.

FIG. 7 shows pulmonary vein (52) after removing the circumferential ablation device assembly subsequent to forming a circumferential lesion (70) around the ablation region of the pulmonary vein wall (53) according to the method shown diagrammatically in FIG. 3 and also in stepwise fashion in FIGS. 4–5. Circumferential lesion (70) is shown located along the pulmonary vein adjacent to the pulmonary vein ostium (54), and is shown to also be "transmural," which is herein intended to mean extending completely through the wall, from one side to the other. Also, the circumferential lesion (70) is shown in FIG. 7 to form a "continuous" circumferential band, which is herein intended to mean without gaps around the pulmonary vein wall circumference, thereby circumscribing the pulmonary vein lumen.

It is believed, however, that circumferential catheter ablation may leave some tissue, either transmurally or along the circumference of the lesion, which is not actually ablated, but which is not substantial enough to allow for the passage of conductive signals. Therefore, the terms "tansmural" and "continuous" as just defined are intended to have "functional" limitations, wherein some tissue in the ablation region may be unablated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein according to the present invention. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 8A:
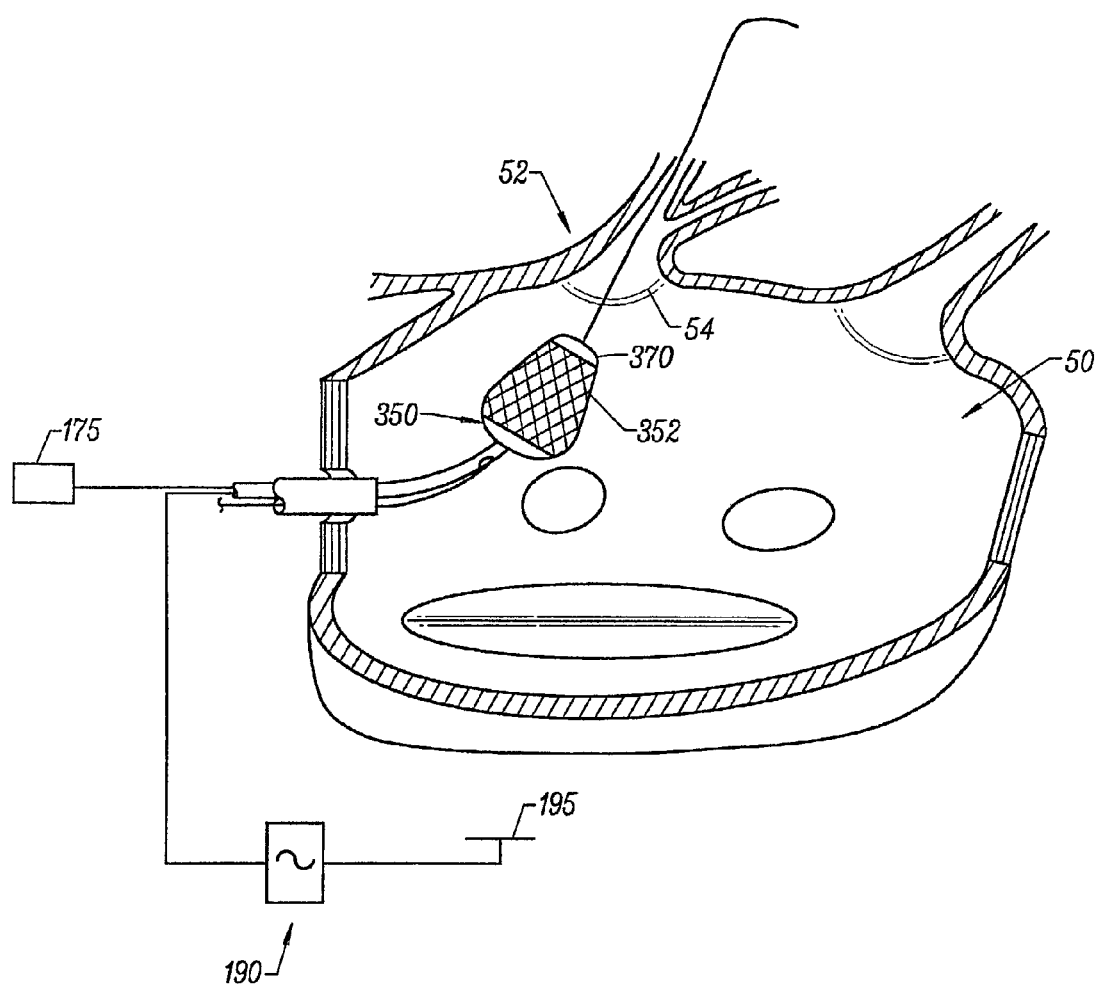
Figure 8B:
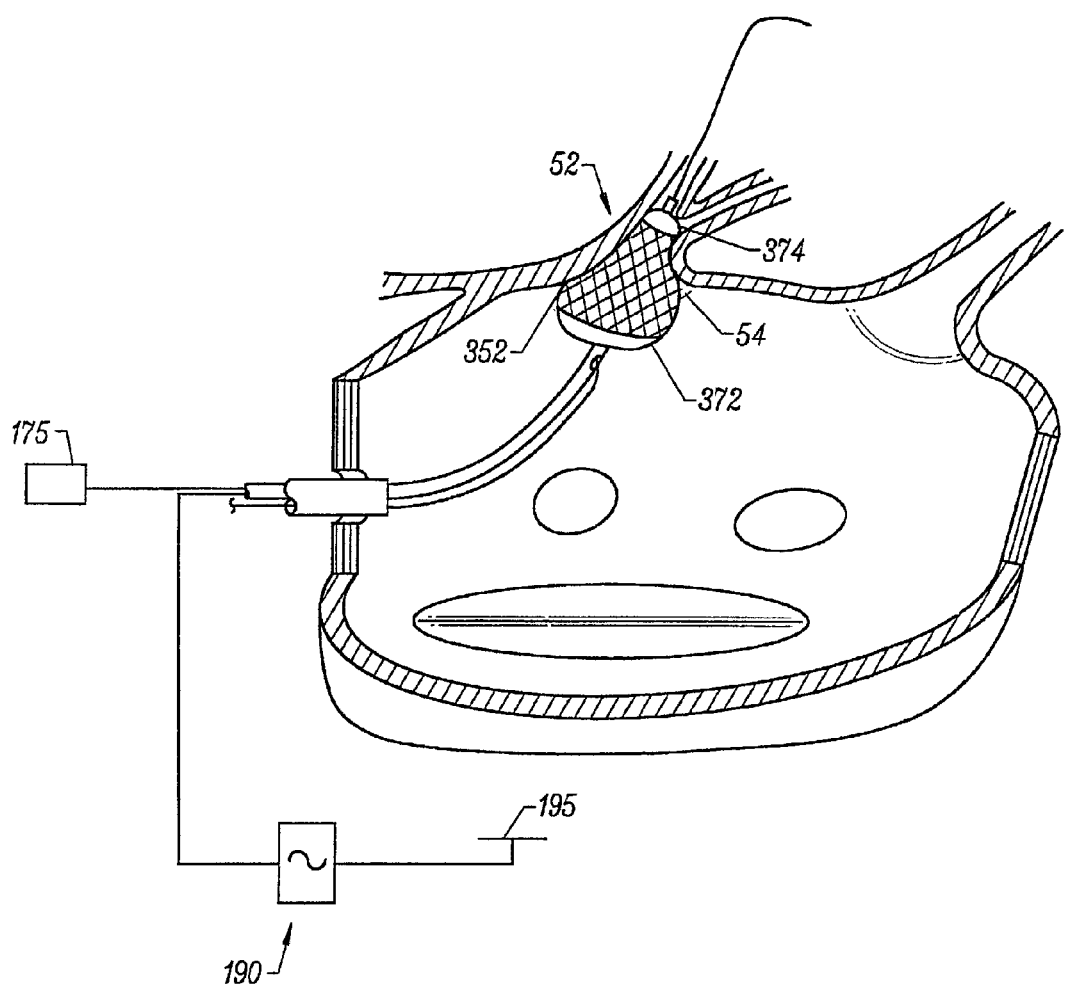
Figure 8C:
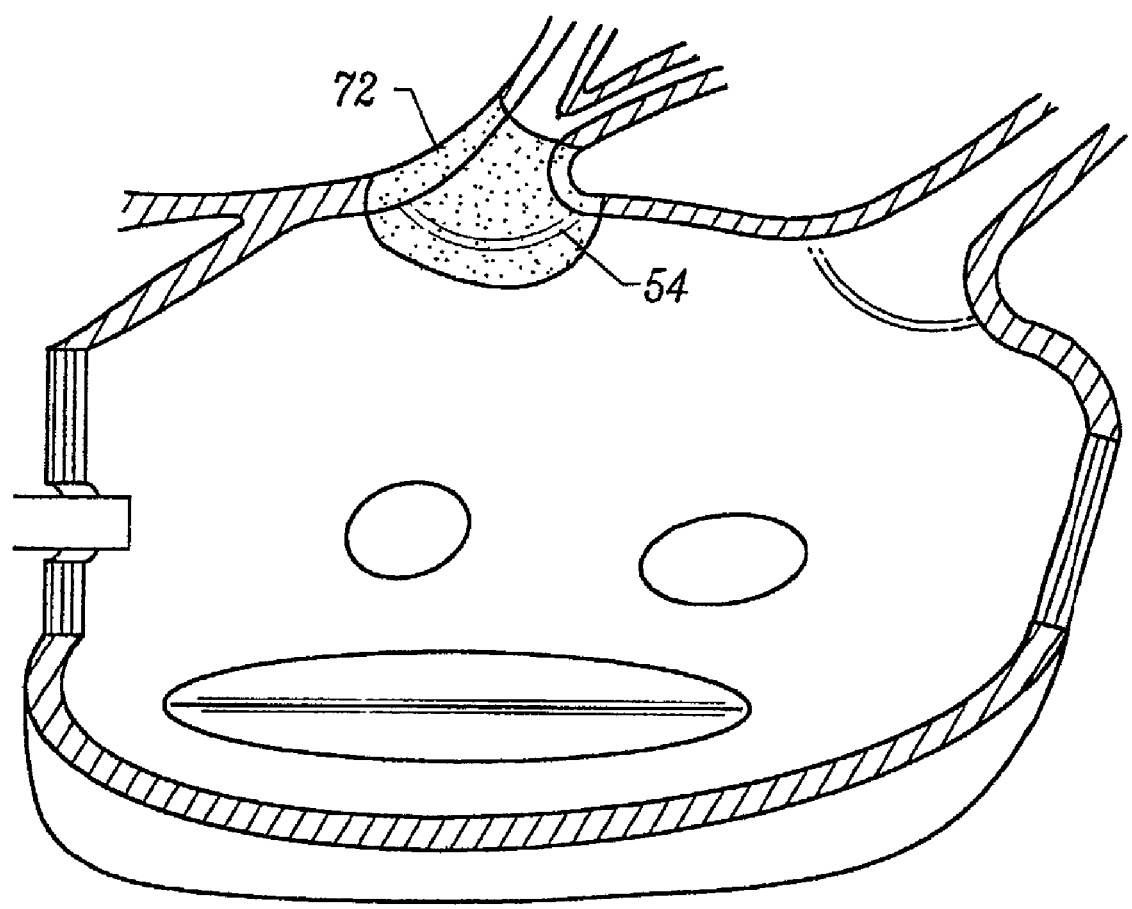
FIG. 8C shows the same perspective view of the left atrium shown in FIGS. 8A–B, although shown after forming a circumferential conduction block according to the circumferential ablation procedure of FIG. 3 and also after removing the circumferential ablation device assembly from the left atrium.

FIGS. 8A–B show a further variation of the present invention, wherein a circumferential ablation member (350) includes a radially compliant expandable member (370) which is adapted to conform to a pulmonary vein ostium (54) at least in part by adjusting it to a radially expanded position while in the left atrium and then advancing it into the ostium. FIG. 8A shows expandable member (370) after being adjusted to a radially expanded position while located in the left atrium (50). FIG. 8B further shows expandable member (370) after being advanced into the pulmonary vein (52) until at least a portion of the expanded working length L of circumferential ablation member (350), which includes a circumferentail ablation element in the form of a circumferential band (352) around expandable member (370), engages the pulmonary vein ostium (54). FIG. 8C shows a portion of a circumferential lesion (72) which forms a circumferential conduction block in the region of the pulmonary vein ostium (54) subsequent to actuating the circumferential ablation element to form the circumferential lesion according to the ablation step shown figuratively in FIG. 8B.

FIGS. 9A–D show a method of using a circumferential ablation device assembly according to the method of FIG. 3 and adjunctively to the formation of long linear lesions in a less-invasive "maze"-type procedure, as introduced above for the treatment of multiwavelet reentrant type fibrillation along the left atrial wall.

Figure 9A:
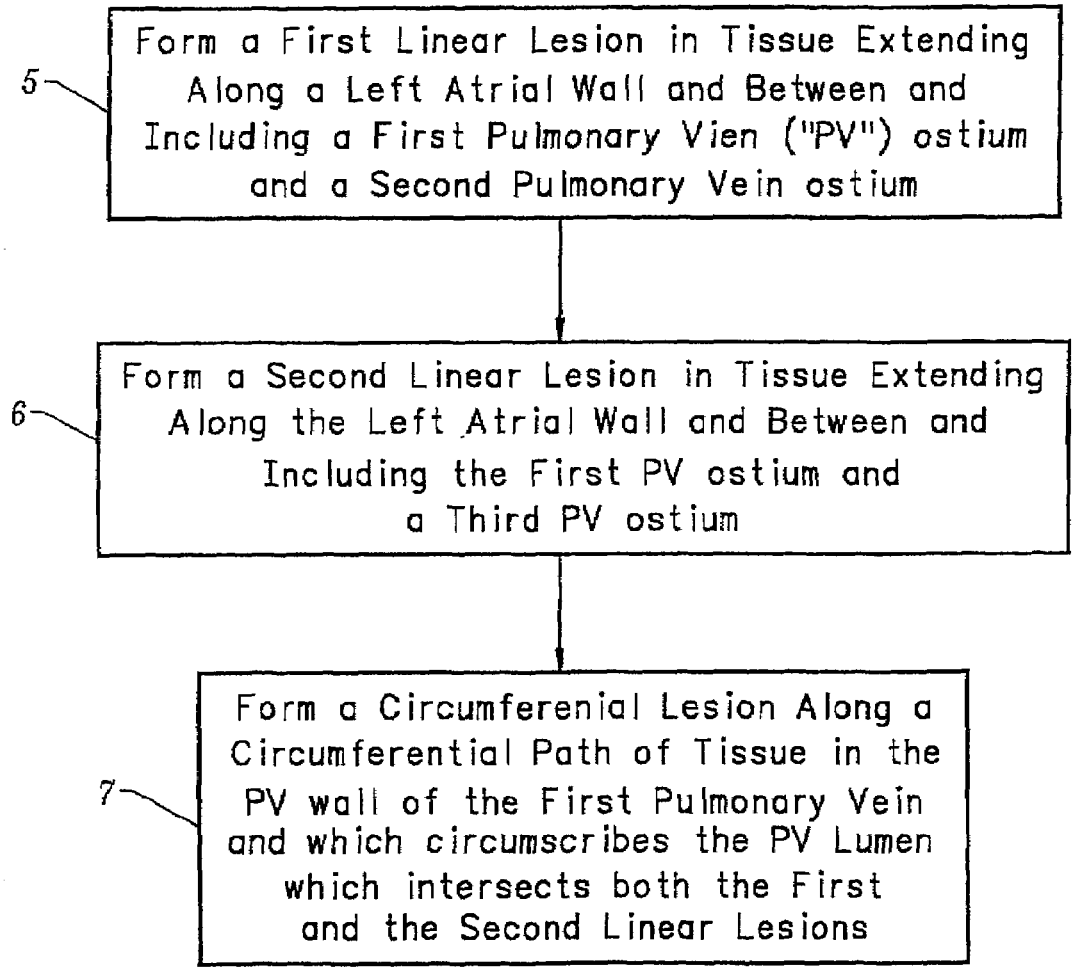
FIG. 9A diagrammatically shows a method for forming a circumferential conduction block according to the method of FIG. 1, although in further combination with a method for forming long linear lesions between pulmonary vein ostia in a less-invasive "maze"-type procedure.

More specifically, FIG. 9A diagrammatically shows a summary of steps of performing the "maze" procedure by forming circumferential conduction blocks that intersect with long linear conduction blocks formed between the pulmonary veins. As disclosed in copending patent application Ser. No. 08/853,861, entitled "Tissue Ablation Device and Method of Use" filed by Michael Lesh, M.D. on May 9, 1997, now U.S. Pat. No. 5,971,983 issued on Oct. 26,1999, which is herein incorporated in its entirety by reference thereto, a box-like conduction block surrounding an arrhythmogenic atrial wall region bounded by the pulmonary veins may be created by forming long linear lesions between anchors in all pairs of adjacent pulmonary vein ostia, such as is shown in part in steps (5) and (6) of FIG. 9A. However, it is further believed that, in some particular applications, such linear lesions may be made sufficiently narrow with respect to the surface area of the pulmonary vein ostia that they may not intersect, thereby leaving gaps between them which may present proarrhythmic pathways for abnormal conduction into and from the box, such as is shown between linear lesions (57,58) in FIG. 9A, and as shown by use of circumferential ablation member (450) in FIG. 9C, the linear lesions are thereby bridged and the gaps are closed.

Figure 9B:
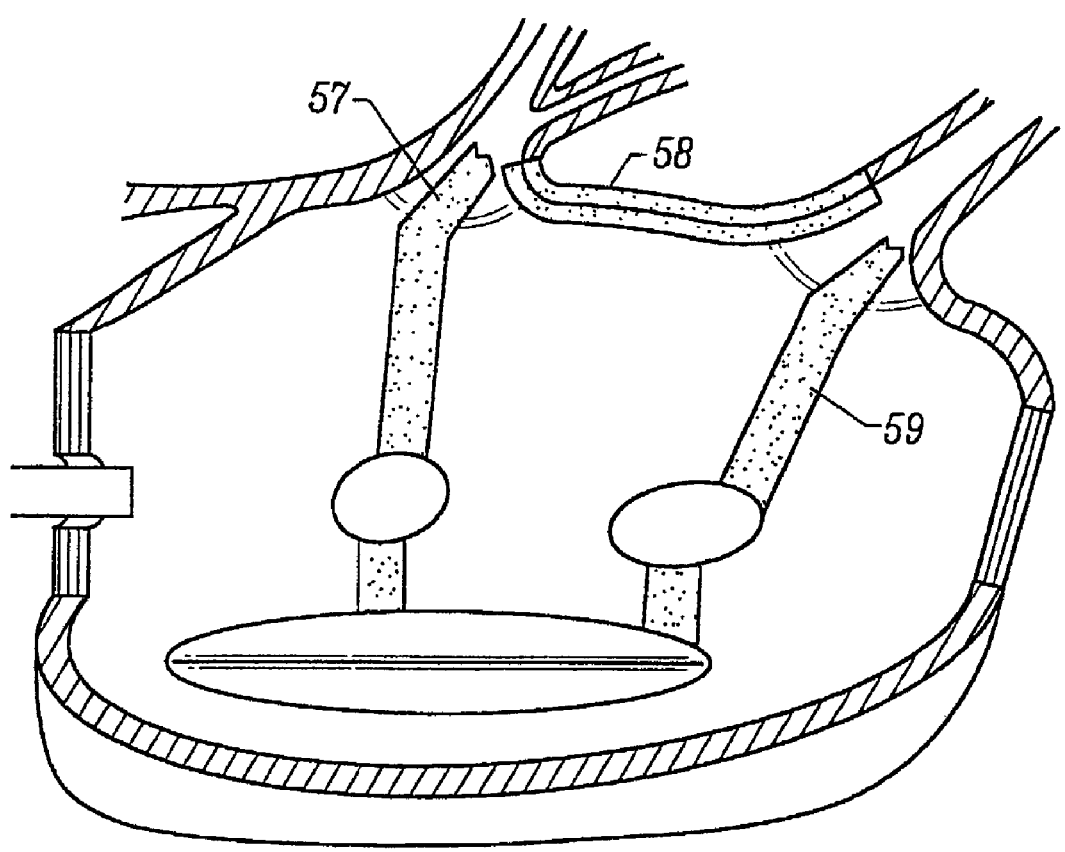
FIG. 9B shows a perspective view of a segmented left atrium after forming several long linear lesions between adjacent pairs of pulmonary vein ostia according to the method of FIG. 9A.
Figure 9C:
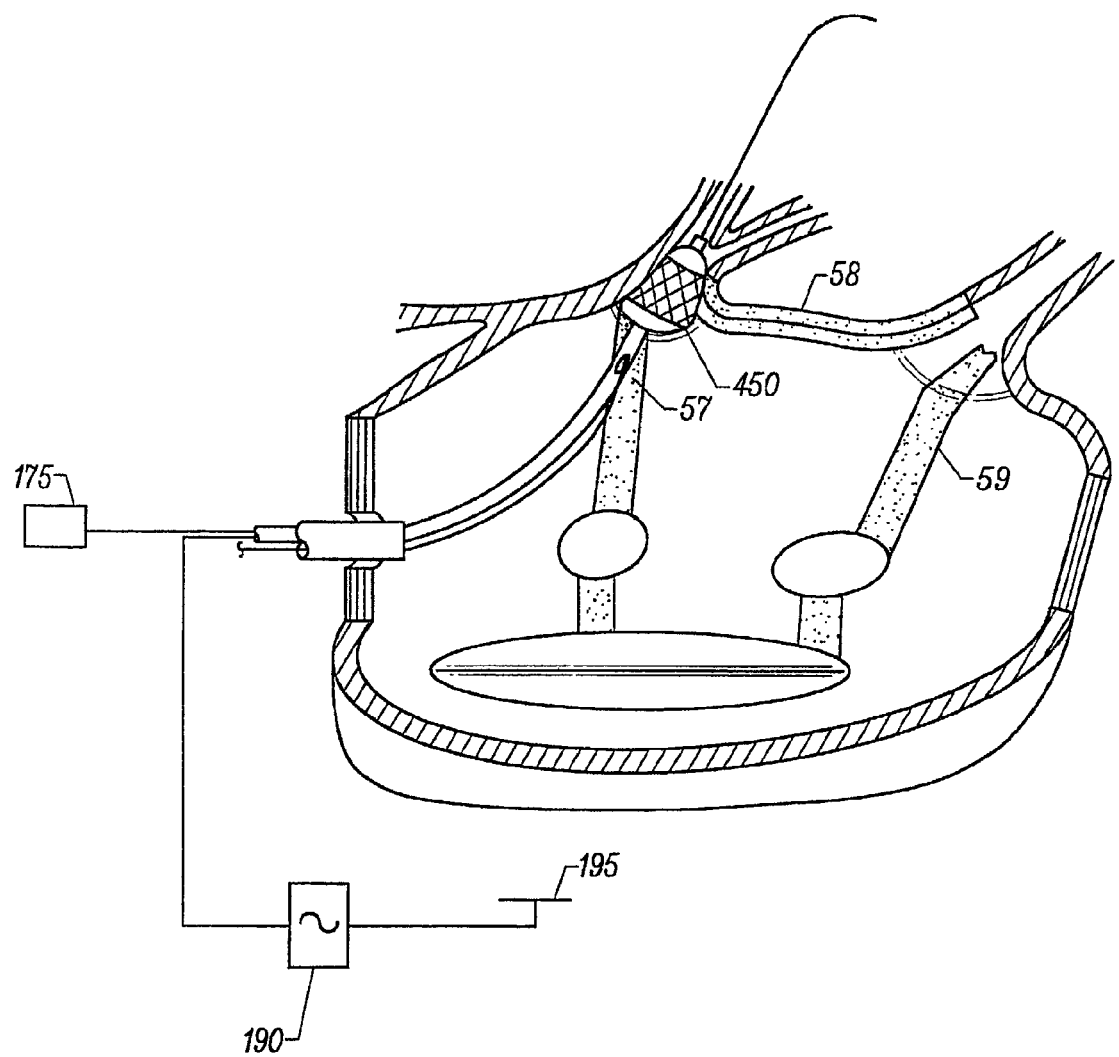
FIG. 9C shows a similar perspective view to that shown in FIG. 9B, although showing a circumferential ablation device during use in forming a circumferential lesion in a pulmonary vein which intersects with two linear lesions that extend into the pulmonary vein, according to the method of FIG. 9A.
Figure 9D:
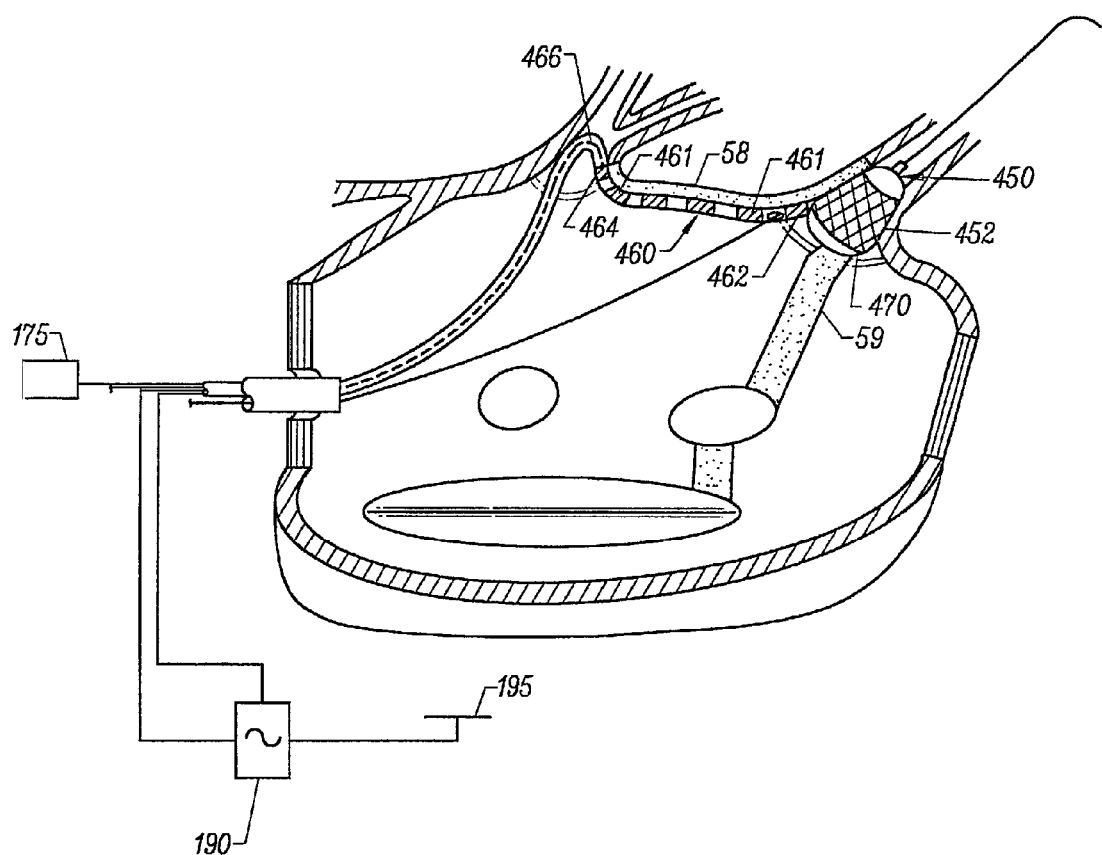
FIG. 9D shows a perspective view of another circumferential ablation catheter for use in forming a circumferential lesion which intersects with at least one linear lesion according to the method of FIG. 9A.

In a further variation to the specific embodiments shown in FIGS. 9B–C, FIG. 9D shows another circumferential ablation device assembly which includes both circumferential and linear ablation elements (452,461), respectively. Circumferential ablation member (450) is shown to include an expandable member (470) which is adjusted to a radially expanded position that is asymmetric to the underlying catheter shaft. Linear ablation member (460) extends along the elongate body proximally from the circumferential ablation member (450). When expanded sufficiently to engage the pulmonary vein wall, expandable member (470) provides at least a portion of an anchor for a first end (462) of linear ablation member (460).

A shaped stylet (466) is shown in shadow in FIG. 9D within the elongate catheter body in the region of the second end (464) of the linear ablation member (460). Shaped stylet (466) is adapted to push the second end (464) into an adjacent pulmonary vein ostium such that the linear ablation member (460) is adapted to substantially contact the left atrial wall between the adjacent vein ostia to form the linear ablation according to the method of FIG. 9A. In addition to the use of shaped stylet (466), it is further contemplated that a second anchor may be used adjacent to second end (464), such as for example an intermediate guidewire tracking member adapted to track over a guidewire engaged to the pulmonary vein.

Figure 9E:
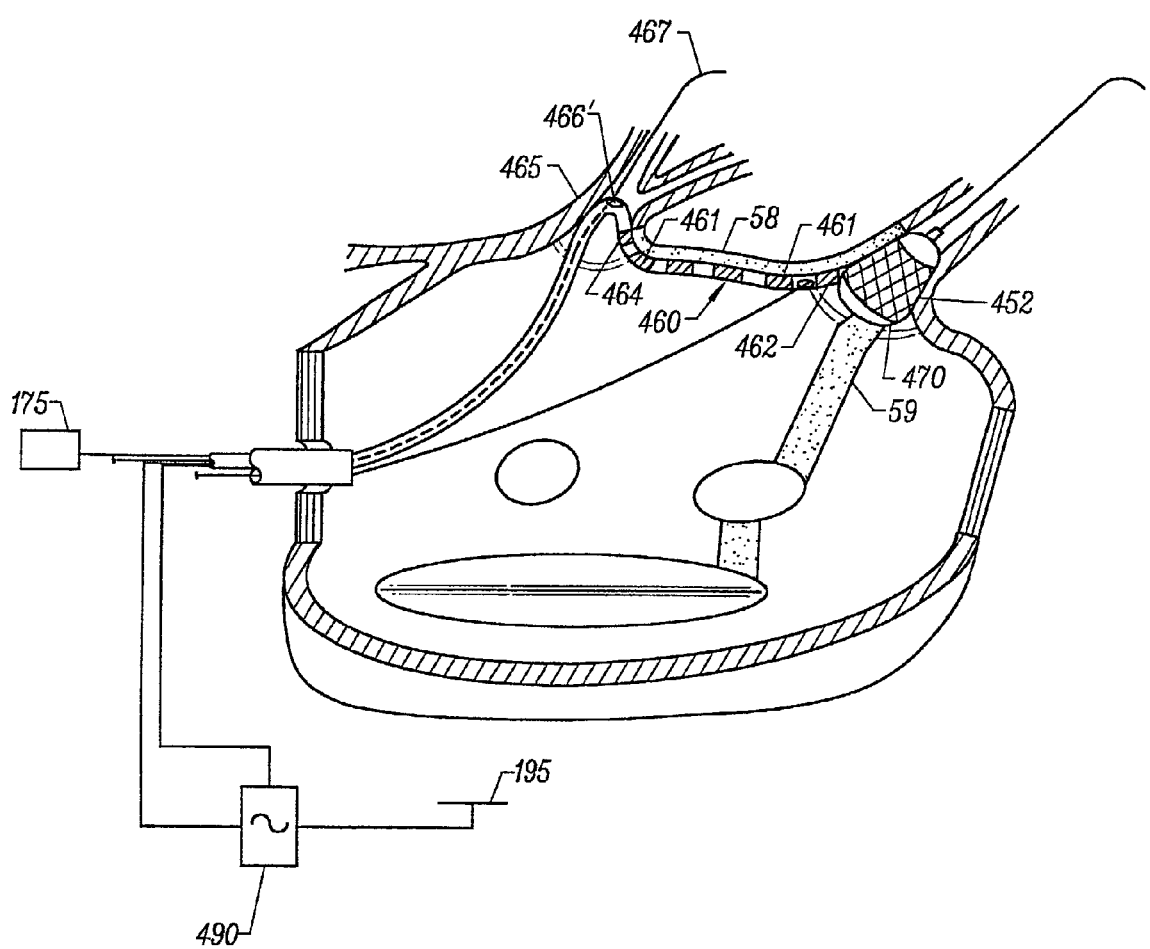
FIG. 9E shows a perspective view of another circumferential ablation catheter for use in forming a circumferential lesion which intersects with at least one linear-lesion according to the method of FIG. 9A.

In a yet a further variation to the specific embodiment shown in FIG. 9D, FIG. 9E shows a circumferential ablation device assembly which includes both circumferential and linear ablation elements (452,460), respectively. Circumferential ablation member (450) is shown to include an expandable member (470) which is adjusted to a radially expanded position that is asymmetric to the underlying catheter shaft. Linear ablation member (460) extends along the elongate body proximally from the circumferential ablation member (450). When expanded sufficiently to engage the pulmonary vein wall, expandable member (470) provides at least a portion of an anchor for a first end (462) of linear ablation member (460).

A shaped stylet (466) is shown in shadow in FIG. 9E within the elongate catheter body in the region of the second end (464) of the linear ablation member (460). Shaped stylet (466) includes a port or opening (465) though which guidewire (469) passes in-order to anchor the second end (464) into an adjacent pulmonary vein ostium such that the linear ablation member (460) is adapted to substantially contact the left atrial wall between the adjacent vein ostia to form the linear ablation according to the method of FIG. 9A. Alternatively to the use of shaped stylet (466) and guidewire (469), it is further contemplated that a second anchor may effected with, for example, an intermediate guidewire tracking member adapted to track over a guidewire (469) engaged to the pulmonary vein.

Figure 10:
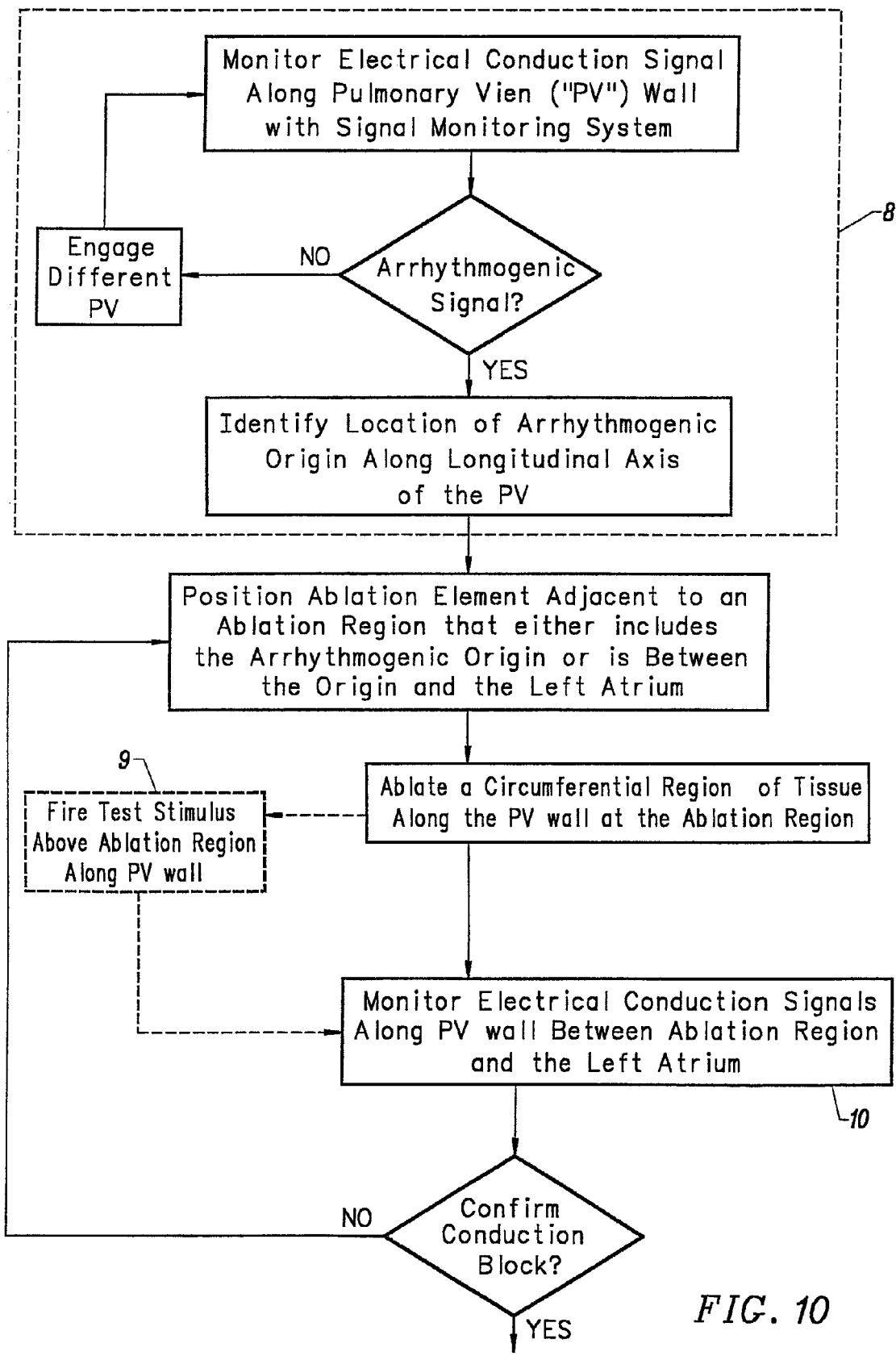
FIG. 10 diagrammatically shows a further method for forming a circumferential conduction block according to the present invention, wherein signal monitoring and "post-ablation" test methods are performed along a pulmonary vein wall in order to locate an arrhythmogenic origin along the wall and to test the efficacy of a circumferential conduction block in the wall, respectively.

FIG. 10 diagrammatically shows a further variation of the method of the present invention which includes, in one aspect, methods for monitoring the electrical signals along the pulmonary vein before and after ablation according to steps (8) and (10), respectively. Signals within the pulmonary vein are monitored prior to forming a conduction block, as indicated in step (8) in FIG. 10, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which information helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored subsequent to circumferential ablation, according to step (10) of the method of FIG. 10. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality) which would potentially identify the need for a subsequent follow-up procedure, such as a second circumferential lesioning procedure in the ablation region.

A test electrode may also be used in a "post ablation" signal monitoring method according to step (10) of FIG. 10. A test stimulus is fired from the test electrode when placed distally or "upstream" of the circumferential lesion in an attempt to simulate a focal arrhythmia. This testing method generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the catheter distal end portion adjacent to the region of the circumferential ablation element, or may be performed using one or more electrodes which form the circumferential ablation element itself.

Circumferential Ablation Member

The expandable members and ablation elements for the various circumferential ablation device assembly embodiments have been previously described generically for the purpose of illustrating in overview fashion how the broad features of the ablation apparatus are adapted for use in performing the methods of the present invention. Examples of more specific embodiments are also contemplated as being suitable for use in the present invention as follows.

Notwithstanding their somewhat schematic detail, the circumferential ablation members show in the previous figures do illustrate a particular embodiment wherein an RF electrode element circumscribes an outer surface of an expandable member. The expandable member of this embodiment may take one of several different forms, although the various Figures show the expandable member as an inflatable balloon which is coupled to an expansion actuator (175) which is a pressurizeable fluid source. The balloon is preferably made of a polymeric material and forms a fluid chamber which communicates with a fluid passageway (not shown in the figures) that extends proximally along the elongate catheter body and terminates proximally in a proximal fluid port that is adapted to couple to the pressurizeable fluid source.

In one expandable balloon variation, the balloon is constructed of a relatively inelastic polymer such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods of the present invention on all needy patients. Therefore, it is further contemplated that a kit of multiple ablation catheters with ablation members having varied predetermined expanded diameters may be provided from which a treating physician may chose a particular device to meet a particular patient's pulmonary vein anatomy.

Further in this regard, a kit may be provided to include a plurality of circumferential ablation device assemblies, where the working length of each expandable member of each circumferential ablation device assembly in the kit has a different expanded outer diameter vis-à-vis all others. A treating physician would measure a diameter of the pulmonary vein lumen at the ablation region where the circumferential conduction block is to be desirably formed, and, based upon the results of the measurement, selecting an appropriate circumferential ablation device from the kit of circumferential ablation devices.

Diameter measurement can be accomplished by injecting contrast material into a body space, e.g. the pulmonary vein, and forming an X-ray image of the body space as the contrast material flows therethrough. A measurement can then be directly made or correlated from the resultant X-ray image of the body space. An alternative measurement technique involves inserting an ultrasound imaging probe into the esophagus of the patient in a region adjacent to the body space to be measured, e.g., the pulmonary vein. A transesophageal ultrasonic image of the pulmonary vein is then performed, and diameter measurement can be accomplished from the ultrasonic image just as described with regard to the X-ray image.

In an alternative expandable balloon variation, the balloon is constructed of a relatively compliant, elastomeric material, such as, for example (but not limited to), a silicone, latex, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as for example a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be Treated with just one or a few devices. Furthermore, this range of diameters is achievable over a relatively low range of pressures, which is believed to diminish a potentially traumatic vessel response that may otherwise be presented concomitant with higher pressure inflations, particularly when the inflated balloon is oversized to the vessel. In addition, the low-pressure inflation feature of this variation is suitable for the present invention because the functional requirement of the expandable balloon is merely to engage the ablation element against a circumferential path along the inner lining of the pulmonary vein wall.

Moreover, a circumferential ablation member is adapted to conform to the geometry of the pulmonary vein ostium, at least in part by providing substantial compliance to the expandable member, as was shown and described previously by reference to FIGS. 8A–B. Further to this conformability to pulmonary vein ostium as provided in the specific design of FIG. 8A–B, the working length L of expandable member (370) is also shown to include a taper which has a distally reducing outer diameter from a proximal end (372) to a distal end (374). In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Further to the RF electrode element as shown variously throughout the previous illustrative Figures, the RF electrode element is coupled to an ablation actuator (190). Ablation actuator (190) generally includes an RF current source (not shown) that is coupled to both the RF electrode element and also a ground patch (195) which is in skin contact with the patient to complete the RF circuit. In addition, ablation actuator (190) preferably includes a monitoring circuit (not shown) and a control circuit (not shown) which together use either the electrical parameters of the RF circuit or tissue parameters such as heat in a feedback control loop during ablation. Also, where a plurality of ablation elements or electrodes in one ablation element are used, a switching means may be used to multiplex the RF current source between the various elements or electrodes. Exemplary frequency and power values for an RF application according to the present invention are around 500 KHz and 50–100 W, respectively.

Figure 11A:
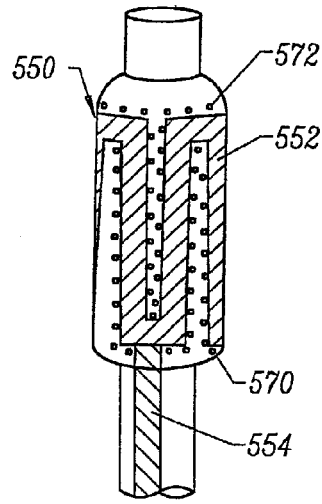
FIGS. 11A–B show perspective views of one particular circumferential ablation member which is adapted for use in performing the method of the present invention, wherein a circumferential ablation electrode is shown to have a secondary shape which is a modified step shape and is shown to form a continuous circumferential electrode band that circumscribes an outer surface of an expandable member wherein in a radially collapsed position and also in a radially expanded position, respectively.
Figure 11B:
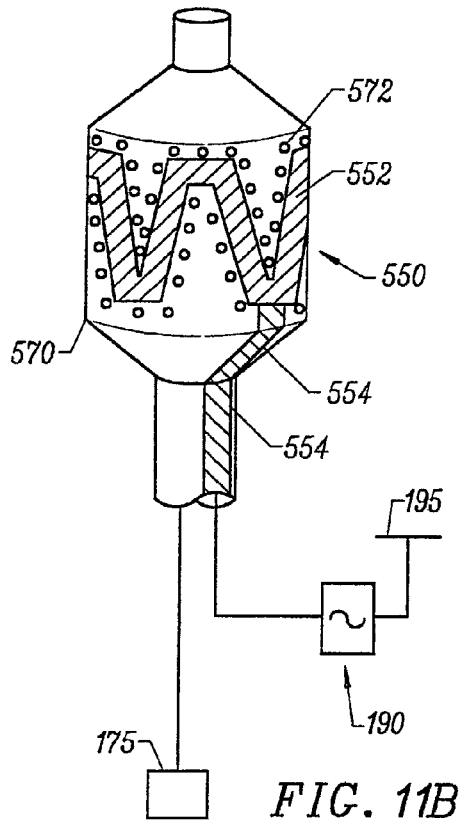
Figure 11C:
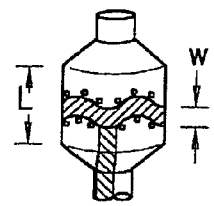
FIGS. 11C–D show perspective views of serpentine and sawtooth shaped circumferential electrode patterns, respectively, each shown to form a continuous equatorial or otherwise circumferentially placed electrode band which circumscribes the working length of an expandable member while it is adjusted to a radially expanded position.
Figure 11D:
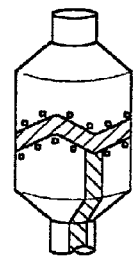

FIGS. 11A–D show various patterns of electrically conductive electrode bands as RF ablation elements which circumscribe an outer surface of the working length of an expandable member. FIGS. 11A–B show circumferential ablation member (550) to include circumferential ablation element (552) which comprises a continuous circumferential electrode band that circumscribes an outer surface of an expandable member (570). FIG. 11B more specifically shows expandable member (570) as a balloon which is fluidly coupled to a pressurizeable fluid source (175), and further shows electrode band (circumferential ablation element) (552), electrically coupled via electrically conductive lead (554) to ablation actuator (190). In addition, a plurality of apertures (572) are shown in the balloon skin wall of expandable member (570) adjacent to electrode band (552). The purpose of these apertures (572) is to provide a positive flow of fluid such as saline or ringers lactate fluid into the tissue surrounding the electrode band (552). Such fluid flow is believed to reduce the temperature rise in the tissue surrounding the electrode element during RF ablation.

The shapes shown collectively in FIGS. 11A–D allow for a continuous electrode band to circumscribe an expandable member's working length over a range of expanded diameters, a feature which is believed to be particularly useful with a relatively compliant balloon as the expandable member. In the particular embodiments of FIGS. 11A–D, this feature is provided primarily by a secondary shape given to the electrode band relative to the longitudinal axis of the working length of the expandable member. Electrode band (552) is thus shown in FIGS. 11A–B to take the specific secondary shape of a modified step curve. Other shapes than a modified step curve are also suitable, such as the serpentine or sawtooth shapes shown respectively in FIGS. 11C–D. Other shapes in addition to those shown in FIGS. 11A–D and which meet the defined functional requirements are further contemplated within the scope of the present invention.

In another aspect of the narrow equatorial band variation for the circumferential ablation element, the circumferential lesion formed may also be relatively narrow when compared to its own circumference, and may be less than two-thirds or even one-half its own circumference on the expandable element when expanded. In one arrangement which is believed to be suitable for ablating circumferential lesions in the pulmonary veins as conduction blocks, the band width w is less than 1 cm, with a circumference on the working length when expanded that is greater than 1.5 cm.

Figure 12A:
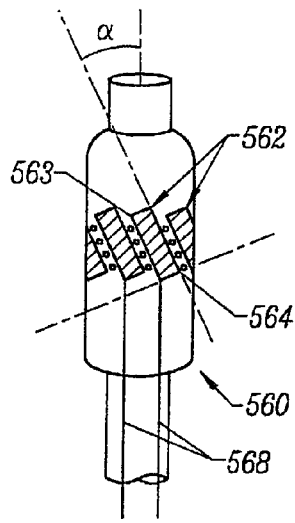
FIGS. 12A–B show perspective views of another circumferential ablation element which includes a plurality of individual ablation electrodes that are spaced circumferentially to form an equatorial or otherwise circumferential band which circumscribes the working length of an expandable member and which is adapted to form a continuous circumferential lesion while the working length is in a radially expanded position.
Figure 12B:
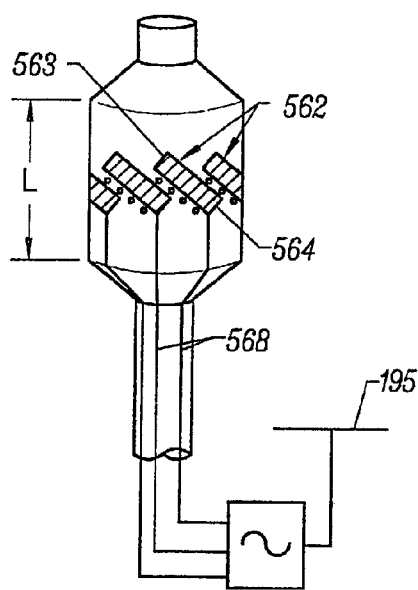

FIGS. 12A–B show a further variation of a circumferential ablation element which is adapted to maintain a continuous circumferential lesion pattern over a range of expanded diameters and which includes electrode elements that form a relatively narrow equatorial band around the working length of an expandable balloon member. In his variation, a plurality of individual electrode elements (562) are included in the circumferential ablation element and are positioned in spaced arrangement along an equatorial band which circumscribes an outer surface of the expandable member's working length L.

The size and spacing between these individual electrode elements (562), when the balloon is expanded, is adapted to form a substantially continuous circumferential lesion in pulmonary vein wall tissue when in intimal contact adjacent thereto, and is further adapted to form such a lesion over a range of band diameters as the working length is adjusted between a variety of radially expanded positions. Each individual electrode element (562) has two opposite ends (563,564), respectively, along a long axis LA and also has a short axis SA, and is positioned such that the long axis LA is at an acute angle relative to the longitudinal axis La of the elongate catheter body and expandable member (560). At least one of the ends (563,564) along the long axis LA overlaps with an end of another adjacent individual electrode element, such that there is a region of overlap along their circumferential aspect, i.e., there is a region of overlap along the circumferential coordinates. The terms "region of overlap along their circumferential coordinates" are herein intended to mean that the two adjacent ends each are positioned along the working length with a circumferential and also a longitudinal coordinate, wherein they share a common circumferential coordinate. In this arrangement, the circumferential compliance along the working length which accompanies radial expansion of the expandable member also moves the individual electrode elements apart along the circumferential axis. However, the spaced, overlapping arrangement described allows the individual electrode elements to maintain a certain degree of their circumferential overlap, or at least remain close enough together, such that a continuous lesion may be formed without gaps between the elements, In addition, the electrode band provided by the circumferential ablation elements shown in FIGS. 11C–D, 12A–B and also shown schematically in FIGS. 4–6B has a band width w relative to the longitudinal axis of the working length which is only required to be sufficiently wide to form a complete conduction block against conduction along the walls of the pulmonary vein in directions parallel to the longitudinal axis. The width of the circumferential ablation element is adapted to ablate a functional width of tissue that will effectively block conduction along the vessel wall in directions parallel to the longitudinal aspect of the vessel in which the ablation element is actuated. In contrast, the working length L of the respective expandable element is adapted to securely anchor the distal end portion in place such that the ablation element is firmly positioned at a selected region of the pulmonary vein for ablation. Accordingly, the width w is relatively narrow compared to the working length L of the expandable element, and the electrode band may thus form a relatively narrow equatorial band which is less than two-thirds or even one-half of the working length of the expandable element. Note that the width is measured by the maximum point to point distance on the circumferential ablation element in a direction parallel to the longitudinal axis of the expandable element, or the ablation catheter, depending on the embodiment. Additionally, it is to be noted here and elsewhere throughout the specification, that a narrow band may be placed at locations other than the equator of the expandable element, preferably as long as the band is bordered on both sides by a portion of the working length L.

The construction for suitable circumferential electrode elements in the RF variation of the present invention, such as the various electrode embodiments described with reference to FIGS. 11A–12B, may comprise a metallic material deposited on the outer surface of the working length using conventional techniques, such as by plasma depositing, sputter coating, chemical vapor deposition, other known techniques which are equivalent for this purpose, or otherwise affixing a metallic shaped member onto the outer surface of the expandable member such as through known adhesive bonding techniques. Other RF electrode arrangements are also considered within the scope of the present invention, so long as they form a circumferential conduction block as previously described. For example, a balloon skin may itself be metallized, such as by mixing conductive metal, including but not limited to gold, platinum, or silver, with a polymer to form a conductive matrix as the balloon skin.

Still further to the broad RF electrode embodiments, another circumferential ablation member variation (not shown) may also include an expandable member, such as an inflatable balloon, that includes a porous skin that is adapted to allow fluid, such as hypertonic saline solution, to pass from an internal chamber defined by the skin and outwardly into surrounding tissues. Such a porous skin may be constructed according to several different methods, such as by forming holes in an otherwise contiguous polymeric material, including mechanically drilling or using laser energy, or the porous skin may simply be an inherently porous membrane. In any case, by electrically coupling the fluid within the porous balloon skin to an RF current source (preferably monopolar), the porous region of the expandable member serves as an RF electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element which may for example be constructed as previously described for the more detailed RF embodiments. However, in the thermal conductor embodiment, such a metallic element would be generally either resistively heated in a closed loop circuit internal to the catheter, or conductively heated by a heat source coupled to the thermal conductor. In the latter case of conductive heating of the thermal conductor with a heat source, the expandable member may be for example a polymeric balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40 deg and 80 deg Celsius.

Further to the thermal conduction variation for the circumferential ablation element, the perfusion balloon embodiment as shown in FIGS. 6A–6B may be particularly useful in such a design. It is believed that ablation through increased temperatures, as provided by example above, may also increase the risk of coagulation of blood in the pulmonary vein adjacent to the expandable member. The use of the perfusion balloon embodiment would reduce the coagulation risk by maintaining blood flow in the area where ablation is performed, thereby preventing a concentration of heat in a stagnant pool of blood.

One further circumferential ablation element design which is believed to be highly useful in performing the methods according to the present invention is shown in FIG. 13 to include a circumferential ablation member (600) with two insulators (602,604) that encapsulate the proximal and distal ends, respectively, of the working length L of an expandable member (610). In the particular embodiment shown, the insulators (602,604) are thermal insulators, such as a thermal insulator comprising a Teflon material. Expandable member (610) is an inflatable balloon which has a balloon-skin (612) that is thermally conductive to surrounding tissue when inflated with a heated fluid such as radiopaque agent or other contrast material, saline fluid, ringers lactate, combinations thereof, other known biocompatible fluids having acceptable heat transfer properties for these purposes, further to the thermal conductor embodiments previously described. By providing these spaced insulators, a circumferential ablation element is formed as an equatorial band (603) of uninsulated balloon skin is located between the opposite insulators. In this configuration, the circumferential ablation member is able to conduct heat externally of the balloon skin much more efficiently at the uninsulated equatorial band/circumferential ablation element (603) than at the insulated portions, and thereby is adapted to ablate only a circumferential region of tissue in a pulmonary vein wall which is adjacent to the equatorial band. It is further noted that this embodiment is not limited to an "equatorial" placement of the ablation element. Rather, a circumferential band may be formed anywhere along the working length of the expandable member and circumscribing the longitudinal axis of the expandable member as previously described.

FIG. 13 further shows use of a radiopaque marker (620) to identify the location of the equatorial band (603) in order to facilitate placement of that band at a selected ablation region of a pulmonary vein via X-ray visualization. Radiopaque marker (620) is opaque under X-ray, and may be constructed for example of a radiopaque metal such as gold, platinum, or tungsten, or may comprise a radiopaque polymer such as a metal loaded polymer. FIG. 13 shows radiopaque marker (620) positioned coaxially over an inner tubular member (621) which is included in a coaxial catheter design as would be apparent to one of ordinary skill. The present invention contemplates the combination of such a radiopaque marker additionally in the other embodiments herein shown and described. To note, when the circumferential ablation member which forms an equatorial or circumferential band includes a metallic electrode element, such electrode may itself be radiopaque and may not require the-use of a separate marker as just described.

The thermal insulator embodiment just described by reference to FIG. 13 is illustrative of a broader embodiment, wherein a circumferential ablation member has an ablating surface along the entire working length of an expandable member, but is shielded from releasing ablative energy into surrounding tissues except for an unshielded or uninsulated equatorial band. As such, the insulator embodiment contemplates other ablation elements, such as the RF embodiments previously described above, which are provided along the entire working length of an expandable member and which are insulated at their ends to selectively ablate tissue only about an uninsulated equatorial band.

In a further example using the insulator embodiment in combination with a circumferential RF electrode embodiment, a metallized balloon which includes a conductive balloon skin may have an electrical insulator, such as a polymeric coating, at each end of the working length and thereby selectively ablate tissue with electricity flowing through the uninsulated equatorial band. In this and other insulator embodiments, it is further contemplated that the insulators described may be only partial and still provide the equatorial band result. For instance, in the conductive RF electrode balloon case, a partial electrical insulator will allow a substantial component of current to flow through the uninsulated portion due to a "shorting" response to the lower resistance in that region.

It is further contemplated that the expandable member of the broad invention may also take forms other than a balloon. For example, FIG. 14 shows an embodiment having an expandable cage (650). Cage (650) comprises coordinating wires (651) and is expandable to engage a desired ablation region in a pulmonary vein.

The radial expansion of cage (650) is accomplished as follows. Sheath (652) is secured around the wires proximally of cage (650). However, core (653), which may be a metallic mandrel such as stainless steel, extends through sheath (652) and distally within cage (650) wherein it terminates in a distal tip (656). Wires (651) are secured to distal tip (656), for example by soldering, welding, adhesive bonding, heat shrinking a polymeric member over the wires, or any combination of these methods. Core (653) is slideable within sheath (652), and may for example be housed within a tubular lumen (not shown) within sheath (652), the wires being housed between a coaxial space between the tubular lumen and sheath (652). By moving the sheath (652) relative to core (653) and distal tip (656)(shown by arrows in FIG. 14), the cage (650) is collapsible along its longitudinal axis in order to force an outward radial bias (also shown with arrows in FIG. 14) to wires (651) in an organized fashion to formed a working length of cage (650) which is expanded (not shown). Alternatively, but not shown, an expandable cage may be formed of superelastic wires which, upon being pushed from a sheath, expand to an enlarged diameter.

Further to the particular expandable cage embodiment shown in FIG. 14, a plurality of ablation electrodes (655) is shown, each being positioned on one of wires (651) and being similarly located along the longitudinal axis of the cage (650). The radial bias given to wires (651) during expansion, together with the location of the ablation electrodes (655), serves to position the plurality of ablation electrodes (655) along a circumferential, equatorial band along the expanded working length of cage (650). The wires forming a cage according to this embodiment may also have another predetermined shape when in the radially expanded position. For example, a taper similar to that shown for expandable member (370) in FIGS. 8A–B may be formed by expanding cage (650), wherein the ablation element formed by ablation electrodes (655) may be positioned between the proximal end and the distal end of the taper.

Further to the construction of the embodiment shown in FIG. 14, wires (651) are preferably metal, and may comprise stainless steel or a superelastic metal alloy, such as an alloy of nickel and titanium, or a combination of both. Regarding the case of nickel and titanium construction for wires (651), a separate electrical conductor may be required in order to actuate ablation electrodes (655) to efficiently emit ablative current into surrounding tissues. In the case where wires (651) are constructed of stainless steel, they may also serve as electrical conductors for ablation electrodes (655). Further to the stainless steel design, the wires (651) may be coated with an electrical insulator to isolate the electrical flow into surrounding tissues at the site of the ablation electrodes (655). Moreover, the ablation electrodes (655) in the stainless steel wire variation may be formed simply by removing electrical insulation in an isolated region to allow for current to flow into tissue only from that exposed region.

In a further cage embodiment (not shown) to that shown in FIG. 14, a circumferential strip of electrodes may also be secured to the cage (650) such that the strip circumscribes the cage at a predetermined location along the cage's longitudinal axis. By expanding cage (650) as previously described, the strip of electrodes are adapted to take a circumferential shape according to the shape of the expanded cage (650). Such an electrode strip is preferably flexible, such that it may be easily reconfigured when the cage is adjusted between the radially collapsed and expanded positions and such that the strip may be easily advanced and withdrawn with the cage within the delivery sheath. Furthermore, the electrode strip may be a continuous circumferential electrode such as a conductive spring coil, or may be a flexible strip which includes several separate electrodes along its circumferential length. In the latter case, the flexible strip may electrically couple all of the electrodes to a conductive lead that interfaces with a drive circuit, or each electrode may be separately coupled to one or more such conductive leads.

Figure 15:
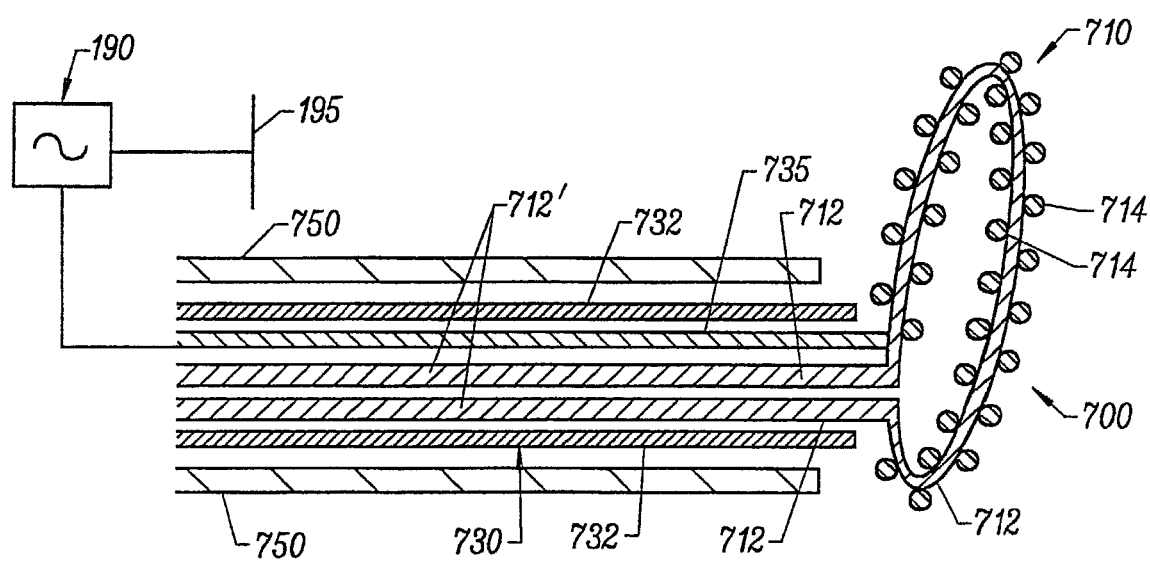
FIG. 15 shows a cross-sectional view of another circumferential ablation member which is adapted for use in the method of the current invention. A superelastic, looped electrode element is shown at the distal end of a pusher and is adapted to circumferentially engage pulmonary vein wall tissue to form a circumferential lesion as a conduction block that circumscribes the pulmonary vein lumen.

Another circumferential ablation element for use in forming a circumferential conduction block according to the present invention is shown in FIG. 15, wherein circumferential ablation member (700) includes a looped member (710) attached, preferably by heat shrinking, to a distal end of a pusher (730). Looped member (710) and pusher (730) are slideably engaged within delivery sheath (750) such that looped member (710) is in a first collapsed position when positioned and radially confined within delivery sheath (750), and expands to a second expanded position when advanced distally from delivery sheath (750).

Looped member (710) is shown in more detail in FIG. 15 to include a core (712) which is constructed of a superelastic metal alloy such as a nickel-titanium alloy and which has a looped portion with shape memory in the looped configuration. This looped configuration is shown in FIG. 15 to be in a plane which is off-axis, preferably perpendicular, to the longitudinal axis of the pusher (730). This off-axis orientation of the loop is adapted to engage a circumferential path of tissue along a pulmonary vein wall which circumscribes the pulmonary vein lumen when the looped member (710) is delivered from the delivery sheath (750) when the delivery sheath is positioned within the vein lumen parallel to its longitudinal axis. An ablation electrode (714) is also shown in FIG. 15 as a metallic coil which is wrapped around core (712) in its looped portion.

Pusher (730) is further shown in FIG. 15 to include a tubular pusher member (732) which is heat shrunk over two ends (712') of core (712) which extend proximally of looped member (710) through pusher (730) in the particular variation shown. While in this embodiment core (712) extends through the pusher in order to provide stiffness to the composite design for the pusher, it is further contemplated that the superelastic metal of the core may be replaced or augmented in the pusher region with another different mandrel or pusher core (not shown), such as a stiffer stainless steel mandrel. Also shown within pusher (730) is an electrically conductive lead (735) which is coupled to the ablation electrode (714) and which is also adapted in a proximal region of the pusher (not shown) to couple to an ablation actuator (190) such as an RF current source (shown schematically).

While particular detailed description has been herein provided for particular embodiments and variations according to the present invention, it is further understood that various modifications, combinations and improvements may be made by one of ordinary skill according to this disclosure and without departing from the broad scope of the invention

The invention claimed is:

1. A method for treating arrhythmia, comprising:
    positioning a radially extendable member at a location where a pulmonary vein extends from an atrium;
    the extendable member having a longitudinal axis and being radially collapsed along the longitudinal axis;
    radially extending the extendable member transverse to the longitudinal axis such that the extendable member in the radially extended condition substantially contacts a circumferential region of tissue at the location and that substantially circumscribes the longitudinal axis; and
    ablating a region of tissue at a location where a pulmonary vein extends from an atrium so as to block electrical communication between cardiac tissue in the pulmonary vein and a region of the atrium that includes other pulmonary veins.

2. A method as recited in claim 1, wherein ablating a region of tissue comprises positioning an ablation element at the region of tissue and activating the ablation element so as to ablate the region of tissue.

3. A method as recited in claim 2, wherein the ablation element is positioned such that the ablated region of tissue lies between a portion of cardiac tissue in the pulmonary vein and the region of the atrium that includes the other pulmonary veins.

4. A method as recited in claim 2, further comprising anchoring the ablation element at the location.

5. A method as recited in claim 4, wherein the ablation element is coupled to the radially extendable member; and
    wherein said anchoring involves engaging a wall of the pulmonary vein with the radially extendable member.

6. A method as recited in claim 5, wherein engaging the wall of the pulmonary vein involves expanding said radially extendable member.

7. A method as recited in claim 6, wherein expanding the radially extending member comprises delivering a pressurized inflation medium to an interior of an inflatable balloon.

8. A method as recited in claim 1, wherein the ablated region of tissue has a circumferential pattern.

9. A method as recited in claim 8, wherein said positioning involves generally locating the ablation element at a generally central position relative to the circumferential pattern of the region of tissue.

10. A method as recited in claim 8, wherein said positioning involves contacting the region of tissue with the ablation element along a substantial portion of the circumferential pattern.

11. A method as recited in claim 1, further comprising substantially removing blood from the location before ablating the region of tissue.

12. A method as recited in claim 11, wherein removing blood comprises inflating an inflatable balloon.

13. A method as recited in claim 11, wherein removing blood comprises inflating at least a first balloon section on a distal side of the ablation element and inflating at least a second balloon section on a proximal side of the ablation element.

14. A method for treating atrial arrhythmia, comprising:
    positioning a radially extendable member at a location where a pulmonary vein extends from an atrium;
    the extendable member having a longitudinal axis and being radially collapsed along the longitudinal axis;
    radially extending the extendable member transverse to the longitudinal axis;
    engaging a pulmonary vein with a radially extendable member on a distal end portion of an ablation device assembly such that the extendable member in the radially extended condition substantially contacts a circumferential region of tissue at the location and that substantially circumscribes the longitudinal axis; and
    ablating a region of cardiac tissue with said ablation device assembly.

15. A method as recited in claim 14, further comprising positioning an ablation element, which is disposed on the distal end portion of the ablation device assembly, at a location where the pulmonary vein extends from a chamber in the heart, wherein ablating a region of cardiac tissue involves ablating tissue adjacent to the ablation element when the ablation element is positioned at the location.

16. A method as recited in claim 15, wherein ablating a region of cardiac tissue comprises ablating an arcuate pattern of tissue that extends about a lumenal axis of the pulmonary vein.

17. A method as recited in claim 16, wherein ablating an arcuate pattern comprises ablating a circumferential pattern.

18. A method as recited in claim 17, wherein the circumferential pattern is formed in a single ablation step.

19. A method as recited in claim 14, wherein ablating a region of tissue comprises ablating a region of tissue that the extendable member engages.

20. A method as recited in claim 14, wherein ablating a region of tissue comprises ablating a region of tissue that lies next to a second region of tissue engaged by the extendable member.

21. A method as recited in claim 14, wherein engaging the pulmonary vein with a radially extendable member comprises expanding an expandable member from a radially collapsed position to a radially expanded position.

22. A method as recited in claim 21, further comprising expanding the expandable member radially outward relative to a longitudinal axis of the distal end portion in all radial directions.

23. A method as recited in claim 21, wherein expanding the expandable member comprises introducing an inflation medium into an interior of an inflatable balloon.

24. A method as recited in claim 14, further comprising removing blood from the location before ablating.

25. A method as recited in claim 24, wherein removing blood comprises inflating an inflatable balloon.

26. A method as recited in claim 24, wherein removing blood comprises inflating at least a first balloon section on a distal side of an ablation element and inflating at least a second balloon section on a proximal side of the ablation element.

27. A method for treating atrial arrhythmia in a heart of a patient, wherein the patient includes a plurality of pulmonary veins and each pulmonary vein extends from a unique location in an atrium of the heart, the method comprising:

positioning a radially extendable member at a location where a pulmonary vein extends from an atrium;

the extendable member having a longitudinal axis and being radially collapsed along the longitudinal axis;

radially extending the extendable member transverse to the longitudinal axis such that the extendable member in the radially extended condition substantially contacts a circumferential region of tissue at the location and that substantially circumscribes the longitudinal axis; and ablating a first ablation lesion that substantially circumscribes only one of the locations.

28. A method as recited in claim 27, further comprising ablating a second ablation lesion that substantially circumscribes only a different one of said locations.

29. A method as recited in claim 28, further comprising forming a linear lesion between the first and second focations to connect the first and second ablation lesions.

30. A method as recited in any one of claims 1, 14, 27, wherein ablating comprises contacting a region of tissue with an ablation element.

31. A method as recited in any one of claims 1, 14, 27, wherein ablating comprises emitting energy from an ablation element.

32. A method as recited in claim 31, wherein ablating comprises emitting energy from at least one electrode ablation element.

* * * * *